(12) United States Patent
Old et al.

(10) Patent No.: US 7,605,178 B2
(45) Date of Patent: Oct. 20, 2009

(54) THERAPEUTIC COMPOUNDS

(75) Inventors: David W. Old, Irvine, CA (US); Vinh X. Ngo, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 76 days.

(21) Appl. No.: 11/774,411

(22) Filed: Jul. 6, 2007

(65) Prior Publication Data

US 2008/0119538 A1    May 22, 2008

Related U.S. Application Data

(60) Provisional application No. 60/806,813, filed on Jul. 10, 2006.

(51) Int. Cl.
*A61K 47/14* (2006.01)
*A61K 31/5575* (2006.01)
*C07C 69/612* (2006.01)

(52) U.S. Cl. .................... 514/529; 514/506; 514/785; 554/117; 554/118; 554/119; 560/8; 560/55

(58) Field of Classification Search ............. 514/506, 514/529, 785; 554/117, 118, 119; 560/8, 560/55
See application file for complete search history.

(56) References Cited

U.S. PATENT DOCUMENTS

| 3,980,700 | A | 9/1976 | Miyano |
| 4,073,799 | A | 2/1978 | Kondo et al. |
| 4,094,886 | A | 6/1978 | Kondo et al. |
| 6,531,485 | B2 | 3/2003 | Cameron et al. |
| 2003/0008895 | A1 | 1/2003 | Cameron et al. |

FOREIGN PATENT DOCUMENTS

| DE | 2359955 | 6/1975 |
| DE | 2608116 | 11/1976 |
| DE | 2708871 | 10/1977 |
| HU | 180705 | 4/1983 |
| HU | 191196 | 1/1987 |
| JP | 51-110557 | 9/1976 |
| JP | 4-149153 | 5/1992 |
| JP | 2001-163779 | 6/2001 |

| WO | WO02/26704 | 4/2002 |
| WO | WO2005/026109 | 3/2005 |
| WO | WO 2006/112742 | * 4/2006 | ............. 554/117 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
XP002461619 Database Caplus/Chemical Abstracts Service (HU191196).
XP002461620 Database Caplus/Chemical Abstracts Service (HU180705).
Kondo, et al., "Synthesis and Nucleophilic Ring-Opening Reactions of Activated Bicyclo-[3.1.0]Hexanes," Tetrahedron Letters (1976) No. 49, pp. 4489-4492.
Kondo, et al., "A New Stereoselective Synthesis of Prostaglandins," Chem, Biochem, Pharmacol. Act. Prostanoids (1979), Pergamon; Oxford, Engl; Meeting Date 1978:185-193.
P. De Clercq, et al., "¹H-NMR Spectral Parameters of Some 1,4-Dihydroxy-2,3-Dialkylcyclopentanes . . . ," Bull. Soc. Chim. Belg. vol. 85/No. 11/1976, pp. 872-882.
P. De Clerq, et al., "Prostaglandin Synthesis Involving Catalytic Hydrogenation . . . ," Tetrahedron (1976) vol. 32, pp. 2747-2752.

* cited by examiner

*Primary Examiner*—Kamal A Saeed
*Assistant Examiner*—Samantha L Shterengarts
(74) *Attorney, Agent, or Firm*—Kevin J. Forrestal; Allergan, Inc.

(57) ABSTRACT

Disclosed herein are compounds of the formula

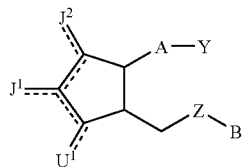

therapeutic methods, compositions, and medicaments related thereto are also disclosed.

19 Claims, No Drawings

THERAPEUTIC COMPOUNDS

RELATED APPLICATION

This application claims the benefit of U.S. Provisional Application Ser. No. 60/806,813, filed Jul. 10, 2006, which is hereby incorporated by reference in its entirety.

DESCRIPTION OF THE INVENTION

Disclosed herein are compounds of the formula

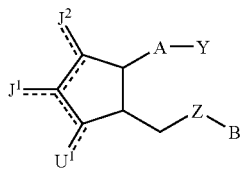

wherein a dashed line represents the presence or absence of a bond;

Y is an organic acid functional group, or an amide or ester thereof comprising up to 14 carbon atoms; or Y is hydroxymethyl or an ether thereof comprising up to 14 carbon atoms; or Y is a tetrazolyl functional group;

A is —$(CH_2)_6$—, cis —$CH_2CH=CH—(CH_2)_3$—, or —$CH_2C\equiv C—(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;

$U^1$ is independently hydrogen; OH; O; S; F; Cl; Br; I; CN; or O-alkyl having 1, 2, 3, 4, 5 or 6 carbon atoms;

$J^1$ and $J^2$ are independently hydrogen; F; Cl; Br; I; O; OH; CN; O-alkyl having 1, 2, 3, 4, 5 or 6 carbon atoms; alkyl having 1, 2, 3, 4, 5, or 6 carbon atoms; or $CF_3$;

Z is S, SO, $SO_2$, NR, NCOR, or $NSO_2R$, wherein R is H or $C_{1-6}$ hydrocarbyl, and B is aryl or heteroaryl.

Also disclosed herein is a carboxylic acid or a bioisostere thereof, said carboxylic acid having a structure

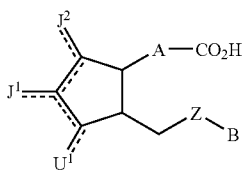

or a pharmaceutically acceptable salt thereof, or a prodrug thereof;

wherein a dashed line represents the presence or absence of a bond;

A is —$(CH_2)_6$—, cis —$CH_2CH=CH—(CH_2)_3$—, or —$CH_2C\equiv C—(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;

$U^1$ is independently hydrogen; OH; O; S; F; Cl; Br; I; CN; or O-alkyl having 1, 2, 3, 4, 5 or 6 carbon atoms;

$J^1$ and $J^2$ are independently hydrogen; F; Cl; Br; I; O; OH; CN; O-alkyl having 1, 2, 3, 4, 5 or 6 carbon atoms; alkyl having 1, 2, 3, 4, 5, or 6 carbon atoms; or $CF_3$;

Z is S, SO, $SO_2$, NR, NCOR, or $NSO_2R$, wherein R is H or $C_{1-6}$ hydrocarbyl, and B is aryl or heteroaryl.

Any structure depicted herein, whether alone or presented with other structures, is contemplated as an individual embodiment.

Furthermore, for each individual structure presented herein, an embodiment is contemplated which comprises the compound of the structure, and/or one or more prodrugs of compounds of the structure, and/or one or more pharmaceutically acceptable salts of the compounds of the structure.

An embodiment is also contemplated which comprises the compound of the structure, and/or one or more pharmaceutically acceptable salts of the compounds of the structure.

An embodiment is also contemplated which comprises the compound of the structure, and/or one or more prodrugs of compounds of the structure.

Since a dashed line represents the presence or absence of a bond, compounds such as those according to the structures below are possible.

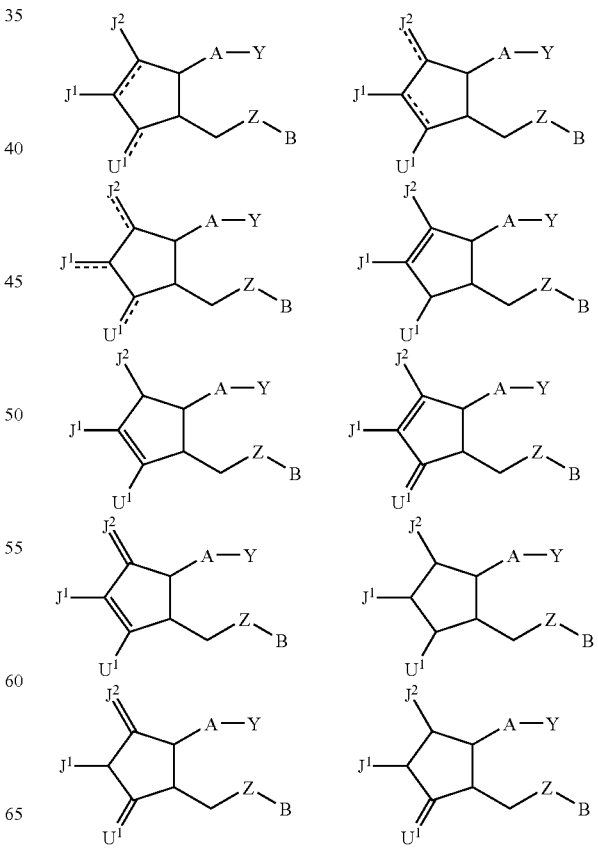

-continued

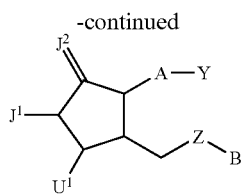

"Bioisosteres are substituents or groups that have chemical or physical similarities, and which produce broadly similar biological properties." Silverman, Richard B., *The Organic Chemistry of Drug Design and Drug Action*, 2$^{nd}$ Edition, Amsterdam: Elsevier Academic Press, 2004, p. 29.

While not intending to be limiting, organic acid functional groups are bioisoteres of carboxylic acids. An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Additionally, an amide or ester of one of the organic acids mentioned above comprising up to 14 carbon atoms is also contemplated. In an ester, a hydrocarbyl moiety replaces a hydrogen atom of an acid such as in a carboxylic acid ester, e.g. CO$_2$Me, CO$_2$Et, etc.

In an amide, an amine group replaces an OH of the acid. Examples of amides include CON(R$^2$)$_2$, CON(OR$^2$)R$^2$, CON(CH$_2$CH$_2$OH)$_2$, and CONH(CH$_2$CH$_2$OH) where R$^2$ is independently H, C$_1$-C$_6$ alkyl, phenyl, or biphenyl. Moieties such as CONHSO$_2$R$^2$ are also amides of the carboxylic acid notwithstanding the fact that they may also be considered to be amides of the sulfonic acid R$^2$—SO$_3$H. The following amides are also specifically contemplated, CONSO$_2$-biphenyl, CONSO$_2$-phenyl, CONSO$_2$-heteroaryl, and CONSO$_2$-naphthyl. The biphenyl, phenyl, heteroaryl, or naphthyl may be substituted or unsubstituted.

Han et. al. (Bioorganic & Medicinal Chemistry Letters 15 (2005) 3487-3490) has recently shown that the groups shown below are suitable bioisosteres for a carboxylic acid. The activity of compounds with these groups in inhibiting HCV NS3 protease was comparable to or superior to similar compounds where the group is replaced by CO$_2$H. Thus, Y could be any group depicted below.

Carboxylic Acid Bioisosteres According to Han et. al.

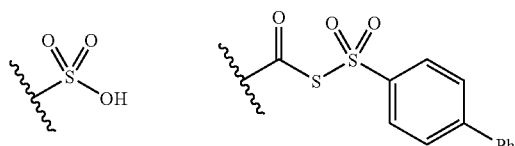

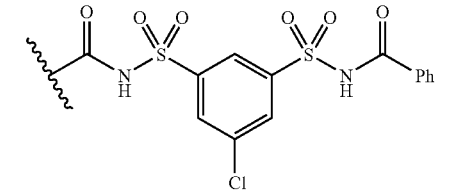

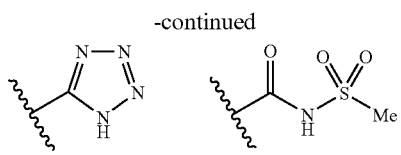

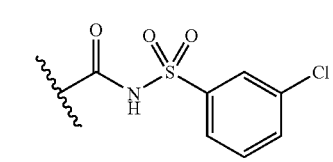

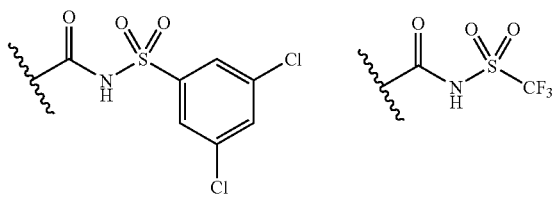

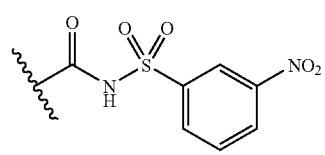

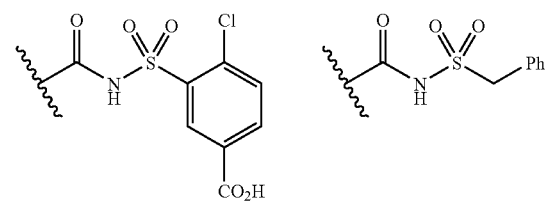

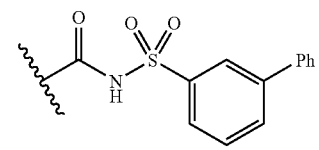

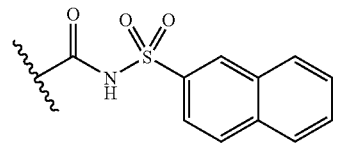

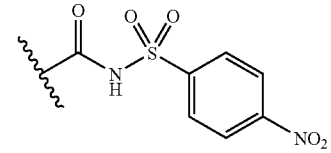

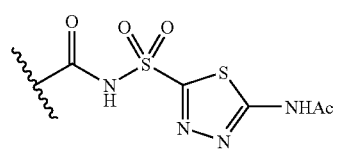

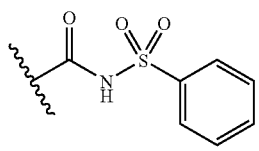

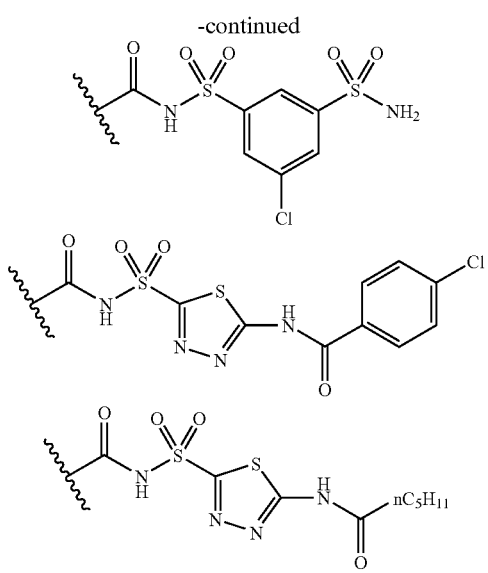

While not intending to limit the scope of the invention in any way, Y may also be hydroxymethyl or an ether thereof comprising up to 14 carbon atoms. An ether is a functional group wherein a hydrogen of an hydroxyl is replaced by carbon, e.g., Y is $CH_2OCH_3$, $CH_2OCH_2CH_3$, etc. These groups are also bioisosteres of a carboxylic acid.

"Up to 14 carbon atoms" means that the entire Y moiety, including the carbonyl carbon of a carboxylic acid ester or amide, and both carbon atoms in the —$CH_2O$—C of an ether has 0, 1, 2, 3, 4, 5, 6, 7, 8, 9, 10, 11, 12, 13, or 14 carbon atoms.

Finally, while not intending to limit the scope of the invention in any way, Y may be a tetrazolyl functional group.

While not intending to be limiting, examples of compounds having the identified Y are depicted below. In these examples R is H or hydrocarbyl, subject to the constraints defined herein. Each structure below represents a specific embodiment which is individually contemplated, as well as pharmaceutically acceptable salts and prodrugs of compounds which are represented by the structures. However, other examples are possible which may not fall within the scope of the structures shown below.

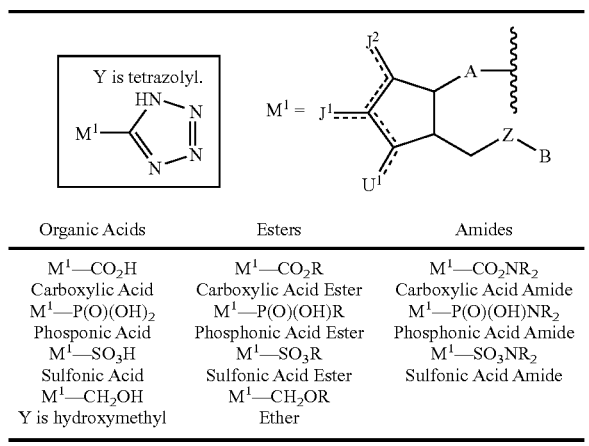

| Organic Acids | Esters | Amides |
|---|---|---|
| $M^1$—$CO_2H$ Carboxylic Acid | $M^1$—$CO_2R$ Carboxylic Acid Ester | $M^1$—$CO_2NR_2$ Carboxylic Acid Amide |
| $M^1$—$P(O)(OH)_2$ Phosponic Acid | $M^1$—$P(O)(OH)R$ Phosphonic Acid Ester | $M^1$—$P(O)(OH)NR_2$ Phosphonic Acid Amide |
| $M^1$—$SO_3H$ Sulfonic Acid | $M^1$—$SO_3R$ Sulfonic Acid Ester | $M^1$—$SO_3NR_2$ Sulfonic Acid Amide |
| $M^1$—$CH_2OH$ Y is hydroxymethyl | $M^1$—$CH_2OR$ Ether | |

A tetrazolyl functional group is another bioisostere of a carboxylic acid. An unsubstituted tetrazolyl functional group has two tautomeric forms, which can rapidly interconvert in aqueous or biological media, and are thus equivalent to one another. These tautomers are shown below.

Additionally, if $R^2$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{12}$ are considered to be within the scope of the term "tetrazolyl."

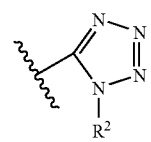

In one embodiment, Y is an organic acid functional group, or an amide or ester thereof comprising up to 14 carbon atoms; or Y is hydroxymethyl or an ether thereof comprising up to 14 carbon atoms; or Y is a tetrazolyl functional group.

In another embodiment, Y is $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

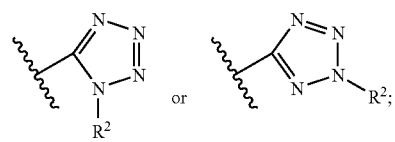

wherein $R^2$ is independently H, $C_1$-$C_6$ alkyl, unsubstituted phenyl, or unsubstituted biphenyl.

According to Silverman (p. 30), the moieties shown below are also bioisosteres of a carboxylic acid.

Carboxylic Acid Bioisosteres According to Silverman

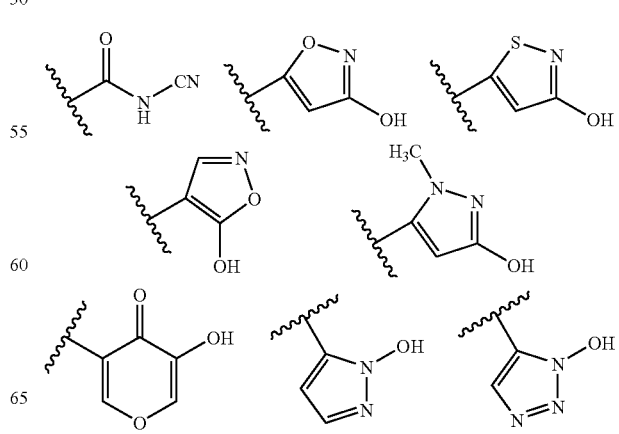

-continued

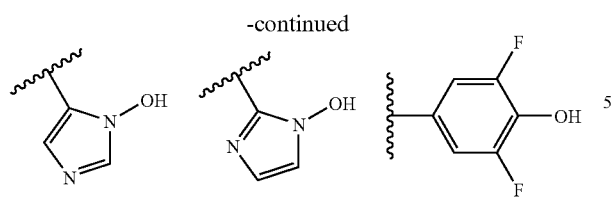

Orlek et al. (*J. Med. Chem.* 1991, 34, 2726-2735) described oxadiazoles as suitable bioisosteres for a carboxylic acid. These ester replacements were shown to be potent muscarinic agonists having improved metabolic stability. Oxadiazoles were also described by Anderson et al. (Eur. J. Med. Chem. 1996, 31, 417-425) as carboxamide replacements having improved in vivo efficacy at the benzodiazepine receptor.

Carboxylic Acid Bioisosteres According to Orlek et. al.

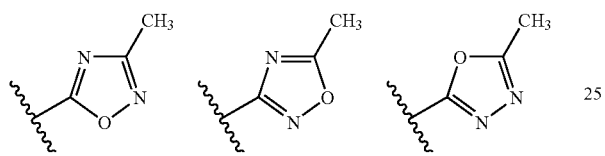

Kohara et al. (*J. Med. Chem.* 1996, 39, 5228-5235) described acidic heterocycles as suitable bioisosteres for a tetrazole. These carboxylic acid replacements were shown to be potent angiotensin II receptor antagonists having improved metabolic stability.

Tetrazole Bioisosteres According to Kohara et. al.

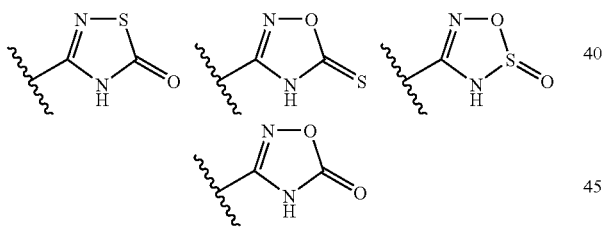

Drysdale et al. (*J. Med. Chem.* 1992, 35, 2573-2581) have described carboxylic acid mimics of non-peptide CCK-B receptor antagonists. The binding affinities of many of the bioisosteres are similar to the parent carboxylic acid.

Carboxylic Acid Bioisosteres According to Drysdale et. al.

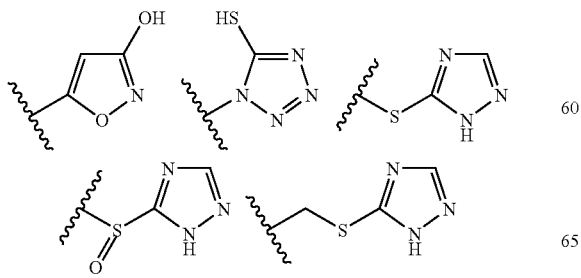

-continued

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O.

While not intending to be limiting, A may be —$(CH_2)_6$—, cis —$CH_2CH$=$CH$—$(CH_2)_3$—, or —$CH_2C$≡$C$—$(CH_2)_3$—.

Alternatively, A may be a group which is related to one of these three moieties in that any carbon is replaced with S or O. For example, A may be a moiety where S replaces one or two carbon atoms such as one of the following or the like.

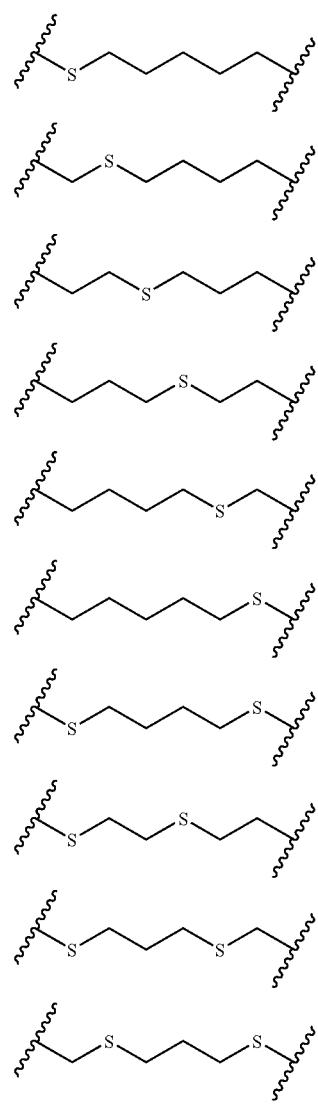

-continued

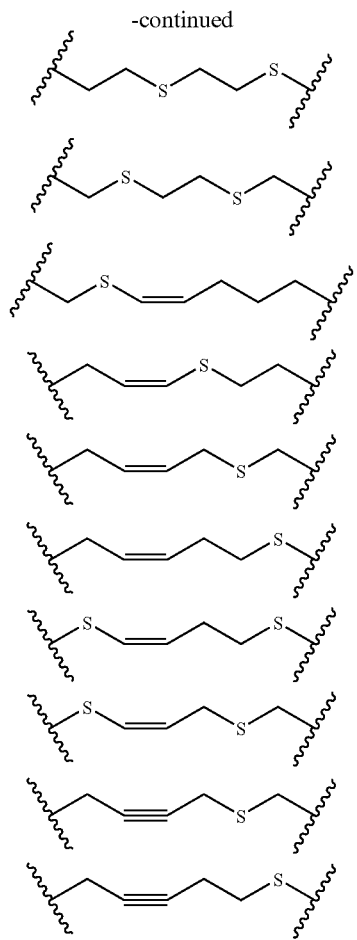

Alternatively, A may be a moiety where O replaces one or two carbon atoms such as one of the following or the like.

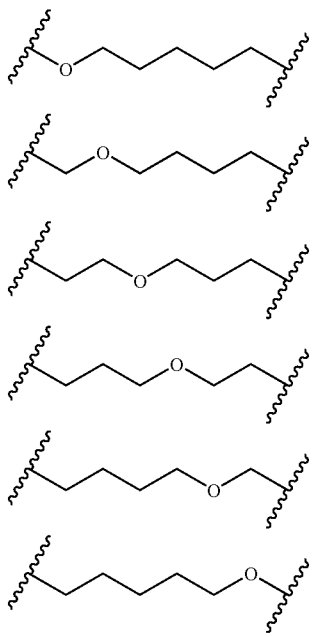

-continued

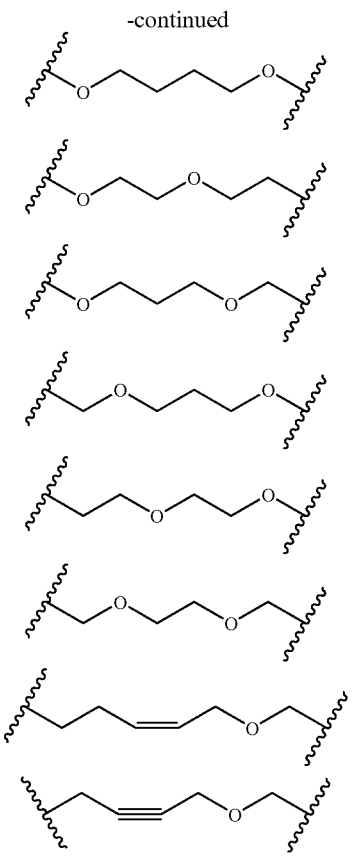

Alternatively, A may have an O replacing one carbon atom and an S replacing another carbon atom, such as one of the following or the like.

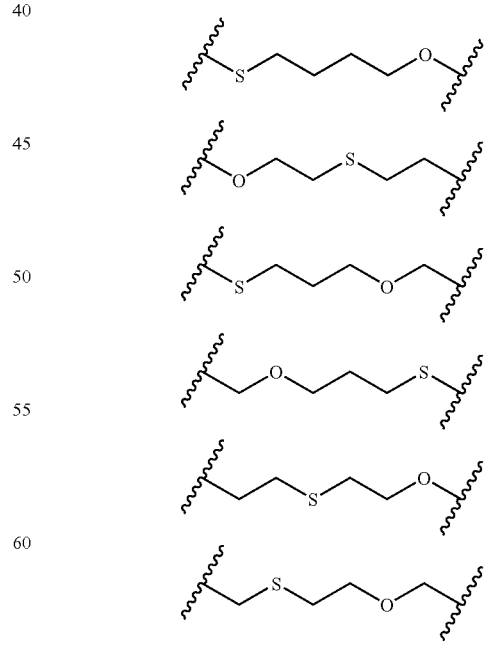

Alternatively, while not intending to limit the scope of the invention in any way, in certain embodiments A is —(CH$_2$)$_m$—Ar—(CH$_2$)$_o$— wherein Ar is interarylene or heterointerarylene, the sum of m and o is 1, 2, 3, or 4, and wherein one CH$_2$ may be replaced with S or O. In other words, while not intending to limit the scope of the invention in any way, in one embodiment A comprises 1, 2, 3, or 4 CH$_2$ moieties and Ar, e.g. —CH$_2$—Ar—, —(CH$_2$)$_2$—Ar—, —CH$_2$—Ar—CH$_2$—, —CH$_2$Ar—(CH$_2$)$_2$—, —(CH$_2$)$_2$—Ar—(CH$_2$)$_2$—, and the like;

in another embodiment A comprises: O; 0, 1, 2, or 3 CH$_2$ moieties; and Ar, e.g., —O—Ar—, Ar—CH$_2$—O—, —O—Ar—(CH$_2$)$_2$—, —O—CH$_2$—Ar—, —O—CH$_2$—Ar—(CH$_2$)$_2$, and the like; or in another embodiment A comprises: S; 0, 1, 2, or 3 CH$_2$ moieties; and Ar, e.g., —S—Ar—, Ar—CH$_2$—S—, —S—Ar—(CH$_2$)$_2$—, —S—CH$_2$—Ar—, —S—CH$_2$—Ar—(CH$_2$)$_2$, —(CH$_2$)$_2$—S—Ar, and the like.

In another embodiment, the sum of m and o is 2, 3, or 4 wherein one CH$_2$ may be replaced with S or O.

In another embodiment, the sum of m and o is 3 wherein one CH$_2$ may be replaced with S or O.

In another embodiment, the sum of m and o is 2 wherein one CH$_2$ may be replaced with S or O.

In another embodiment, the sum of m and o is 4 wherein one CH$_2$ may be replaced with S or O.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$-Ph-. While not intending to limit scope of the invention in any way, substituents may have 4 or less heavy atoms, wherein the heavy atoms are C, N, O, S, P, F, Cl, Br, and/or I in any stable combination. Any number of hydrogen atoms required for a particular substituent will also be included. A substituent must be stable enough for the compound to be useful as described herein. In addition to the atoms listed above, a substituent may also have a metal cation or any other stable cation having an atom not listed above if the substituent is acidic and the salt form is stable. For example, —OH may form an —O$^-$Na$^+$ salt or CO$_2$H may form a CO$_2^-$K$^+$ salt. Any cation of the salt is not counted in the "4 or less heavy atoms." Thus, the substituent may be hydrocarbyl having up to 4 carbon atoms, including alkyl up to C$_4$, alkenyl, alkynyl, and the like;

hydrocarbyloxy up to C$_3$;

organic acid such as CO$_2$H, SO$_3$H, P(O)(OH)$_2$, and the like, and salts thereof;

CF$_3$;

halo, such as F, Cl, or Br;

hydroxyl;

NH$_2$ and alkylamine functional groups up to C$_3$;

other N or S containing substituents such as CN, NO$_2$, and the like;

and the like.

In one embodiment A is —(CH$_2$)$_m$-Ph-(CH$_2$)$_o$— wherein the sum of m and o is 1, 2, or 3, and wherein one CH$_2$ may be replaced with S or O.

In another embodiment A is —CH$_2$—Ar—OCH$_2$—. In another embodiment A is —CH$_2$-Ph-OCH$_2$—. In another embodiment, Ph is attached at the 1 and 3 positions, otherwise known as m-interphenylene, such as when A has the structure shown below.

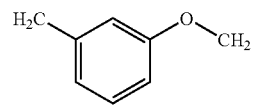

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph- wherein one CH$_2$ may be replaced with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph-.

In other embodiments, A has one of the following structures, where Y is attached to the aromatic or heteroaromatic ring.

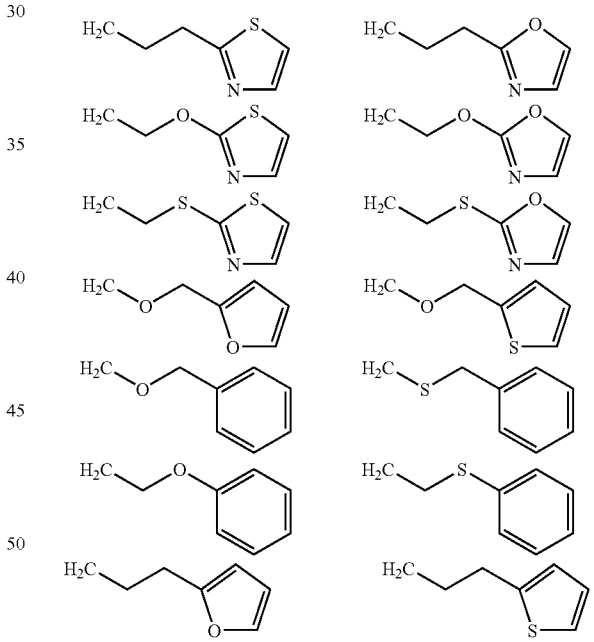

In another embodiment A is —CH$_2$OCH$_2$Ar.
In another embodiment A is —CH$_2$SCH$_2$Ar.
In another embodiment A is —(CH$_2$)$_3$Ar.
In another embodiment A is —CH$_2$O(CH$_2$)$_4$.
In another embodiment A is —CH$_2$S(CH$_2$)$_4$.
In another embodiment A is —(CH$_2$)$_6$—.
In another embodiment A is cis —CH$_2$CH=CH—(CH$_2$)$_3$—.
In another embodiment A is —CH$_2$C≡C—(CH$_2$)$_3$—.
In another embodiment A is —S(CH$_2$)3S(CH$_2$)$_2$—.
In another embodiment A is —(CH$_2$)$_4$OCH$_2$—.

In another embodiment A is cis —CH₂CH═CH—CH₂OCH₂—.

In another embodiment A is —CH₂CH≡CH—CH₂OCH₂—.

In another embodiment A is —(CH₂)₂S(CH₂)3-.

In another embodiment A is —CH₂-Ph-OCH₂—, wherein Ph is interphenylene,

In another embodiment A is —CH₂-mPh-OCH₂—, wherein mPh is m-interphenylene.

In another embodiment A is —CH₂—O—(CH₂)₄—.

In another embodiment A is —CH₂—O—CH₂—Ar—, wherein Ar is 2,5-interthienylene.

In another embodiment A is —CH₂—O—CH₂—Ar—, wherein Ar is 2,5-interfurylene.

In another embodiment A is (3-methylphenoxy)methyl.
In another embodiment A is (4-but-2-ynyloxy)methyl.
In another embodiment A is 2-(2-ethylthio)thiazol-4-yl.
In another embodiment A is 2-(3-propyl)thiazol-5-yl.
In another embodiment A is 3-methoxymethyl)phenyl.
In another embodiment A is 3-(3-propylphenyl.
In another embodiment A is 3-methylphenethyl.
In another embodiment A is 4-(2-ethyl)phenyl.
In another embodiment A is 4-phenethyl.
In another embodiment A is 4-methoxybutyl.
In another embodiment A is 5-(methoxymethyl)furan-2-yl.
In another embodiment A is 5-(methoxymethyl)thiophen-2-yl.
In another embodiment A is 5-(3-propyl)furan-2-yl.
In another embodiment A is 5-(3-propyl)thiophen-2-yl.
In another embodiment A is 6-hexyl.
In another embodiment A is (Z)-6-hex-4-enyl.

Compounds according to the each of the structures depicted below are possible.

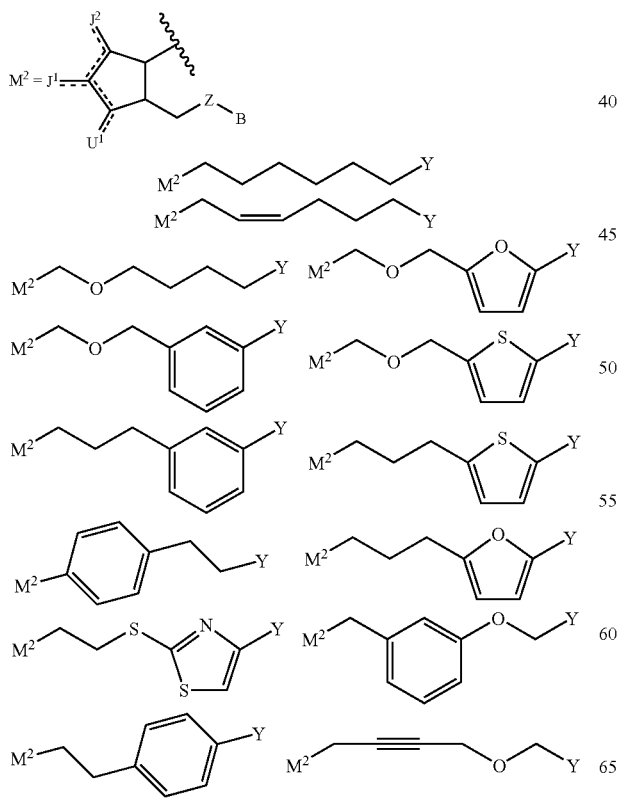

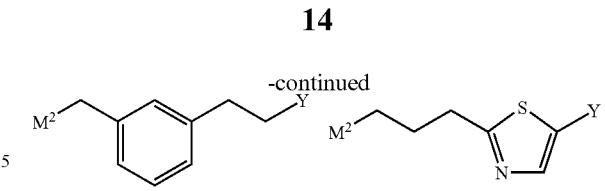

$U^1$ is independently O; S; F; Cl; Br; I; CN; or O-alkyl having 1, 2, 3, 4, 5 or 6 carbon atoms.

In one embodiment, $U^1$ is hydrogen.
In one embodiment, $U^1$ is OH.
In one embodiment, $U^1$ is O.
In one embodiment, $U^1$ is S.
In one embodiment, $U^1$ is F.
In one embodiment, $U^1$ is Cl.
In one embodiment, $U^1$ is Br.
In one embodiment, $U^1$ is I.
In one embodiment, $U^1$ is CN.
In one embodiment, $U^1$ is O-alkyl having 1, 2, 3, 4, 5 or 6 carbon atoms.

$J^1$ and $J^2$ are independently hydrogen; F; Cl, Br; I; O; OH; CN; O-alkyl having 1, 2, 3, 4, 5 or 6 carbon atoms; alkyl having 1, 2, 3, 4, 5, or 6 carbon atoms; or $CF_3$.

In one embodiment, $J^1$ is hydrogen.
In one embodiment, $J^1$ is F.
In one embodiment, $J^1$ is Cl.
In one embodiment, $J^1$ is Br.
In one embodiment, $J^1$ is I.
In one embodiment, $J^1$ is O.
In one embodiment, $J^1$ is OH.
In one embodiment, $J^1$ is CN.
In one embodiment, $J^1$ is O-alkyl having 1, 2, 3, 4, 5 or 6 carbon atoms.
In one embodiment, $J^1$ is alkyl having 1, 2, 3, 4, 5, or 6 carbon atoms.
In one embodiment, $J^1$ is $CF_3$.
In one embodiment, $J^2$ is hydrogen.
In one embodiment, $J^2$ is F.
In one embodiment, $J^2$ is Cl.
In one embodiment, $J^2$ is Br.
In one embodiment, $J^2$ is I.
In one embodiment, $J^2$ is O.
In one embodiment, $J^2$ is OH.
In one embodiment, $J^2$ is CN.
In one embodiment, $J^2$ is O-alkyl having 1, 2, 3, 4, 5 or 6 carbon atoms.
In one embodiment, $J^2$ is alkyl having 1, 2, 3, 4, 5, or 6 carbon atoms.
In one embodiment, $J^2$ is $CF_3$.

Thus, compounds according to the structures shown below are possible.

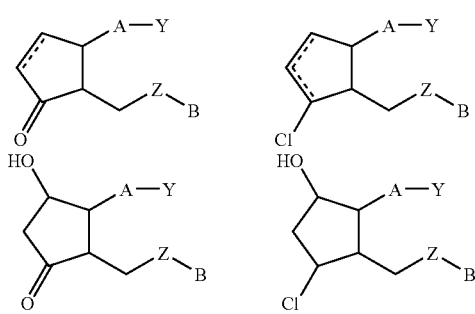

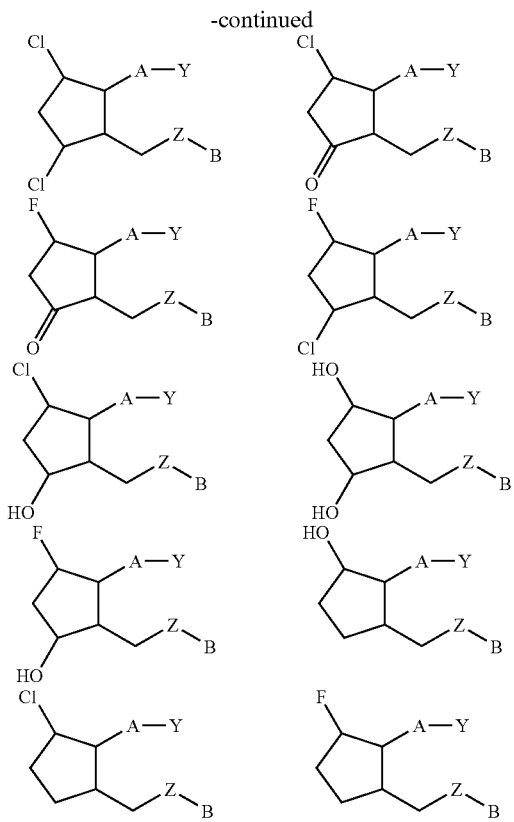

Z is S, SO, SO$_2$, NR, NCOR, or NSO$_2$R, wherein R is H or C$_{1-6}$ hydrocarbyl.

Thus, compounds such as shown below are possible.

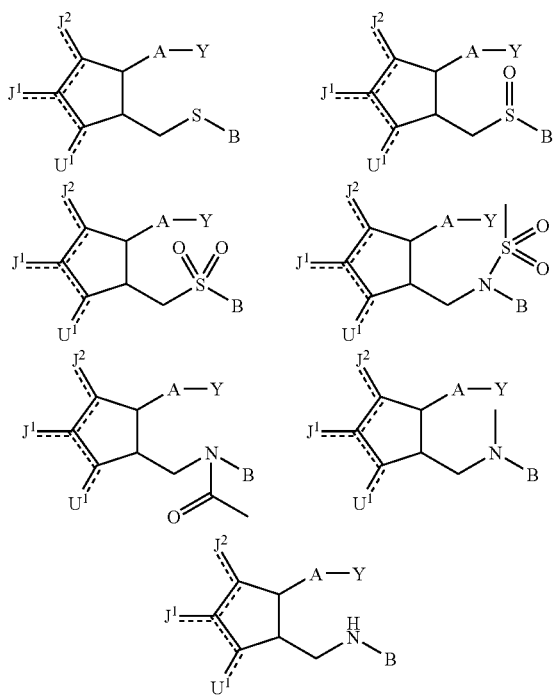

In one embodiment, Z is S.
In another embodiment, Z is NH.
In another embodiment, Z is SO.
In another embodiment, Z is SO$_2$.
In another embodiment, Z is NCH$_3$.
In another embodiment, Z is NC$_2$H$_5$.
In another embodiment, Z is NC$_3$H$_7$.
In another embodiment, Z is NC$_4$H$_9$.
In another embodiment, Z is NC$_5$H$_{11}$.
In another embodiment, Z is NC$_6$H$_{13}$.
In another embodiment, Z is N-phenyl.
In another embodiment, Z is NSO$_2$CH$_3$.
In another embodiment, Z is NCOCH$_3$.

B is aryl or heteroaryl.

Aryl is an aromatic ring or ring system such as phenyl, naphthyl, biphenyl, and the like.

Heteroaryl is aryl having one or more N, O, or S atoms in the ring, i.e. one or more ring carbons are substituted by N, O, and/or S. While not intending to be limiting, examples of heteroaryl include thienyl, pyridinyl, furyl, benzothienyl, benzofuryl, imidizololyl, indolyl, and the like.

A substituent of aryl or heteroaryl may have up to 20 non-hydrogen atoms each in any stable combination and as many hydrogen atoms as necessary, wherein the non-hydrogen atoms are C, N, O, S, P, F, Cl, Br, and/or I in any stable combination. However, the total number of non-hydrogen atoms on all of the substituents combined must also be 20 or less. A substituent must be sufficiently stable for the compound to be useful as described herein. In addition to the atoms listed above, a substituent may also have a metal cation or other stable cation having an atom not listed above if the substituent is acidic and the salt form is stable. For example, —OH may form an —O$^-$Na$^+$ salt or CO$_2$H may form a CO$_2^-$K$^+$ salt. Any cation of the salt is not counted in the 20 non-hydrogen atoms. Thus, while not intending to limit the scope of the invention in any way, a substituent may be:

hydrocarbyl, i.e. a moiety consisting of only carbon and hydrogen such as alkyl, alkenyl, alkynyl, and the like, including linear, branched or cyclic hydrocarbyl, and combinations thereof;

hydrocarbyloxy, meaning O-hydrocarbyl such as OCH$_3$, OCH$_2$CH$_3$, O-cyclohexyl, etc, up to 19 carbon atoms;

other ether substituents such as CH$_2$OCH$_3$, (CH$_2$)$_2$OCH(CH$_3$)$_2$, and the like;

thioether substituents including S-hydrocarbyl and other thioether substituents;

hydroxyhydrocarbyl, meaning hydrocarbyl-OH such as CH$_2$OH, C(CH$_3$)$_2$OH, etc, up to 19 carbon atoms;

nitrogen substituents such as NO$_2$, CN, and the like, including amino, such as NH$_2$, NH(CH$_2$CH$_3$OH), NHCH$_3$, and the like;

carbonyl substituents, such as CO$_2$H, ester, amide, and the like;

halogen, such as chloro, fluoro, bromo, and the like fluorocarbyl, such as CF$_3$, CF$_2$CF$_3$, etc.;

phosphorous substituents, such as PO$_3^{2-}$, and the like;

sulfur substituents, including S-hydrocarbyl, SH, SO$_3$H, SO$_2$-hydrocarbyl, SO$_3$-hydrocarbyl, and the like.

Substituted aryl or heteroaryl may have as many substituents as the ring or ring system will bear, and the substituents may be the same or different. Thus, for example, an aryl ring or a heteroaryl ring may be substituted with chloro and methyl; methyl, OH, and F; CN, NO$_2$, and ethyl; and the like including any conceivable substituent or combination of substituent possible in light of this disclosure.

Substituted aryl or substituted heteroaryl also includes a bicyclic or polycyclic ring system wherein one or more rings are aromatic and one or more rings are not. For example, indanonyl, indanyl, indanolyl, tetralonyl, and the like are substituted aryl and are also substituted phenyl. For this type of polycyclic ring system, an aromatic or heteroaromatic ring, not a non-aromatic ring, must be attached to the remainder of the molecule, i.e. the part of the molecule that is not B. In other words, in any structure depicting —B herein, where — is a bond, the bond is a direct bond to an aromatic ring.

Another embodiment is a compound according to the structure

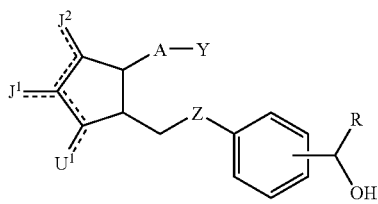

or a pharmaceutical salt thereof, or a prodrug thereof, wherein R is hydrogen or $C_{1-10}$ hydrocarbyl.

Another embodiment is a compound according to the structure

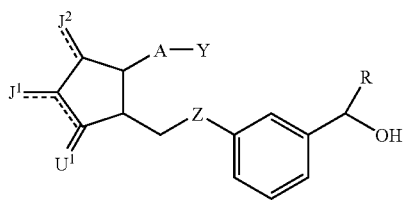

or a pharmaceutical salt thereof, or a prodrug thereof, wherein R is hydrogen or $C_{1-10}$ hydrocarbyl.

Another embodiment is a compound according to the structure

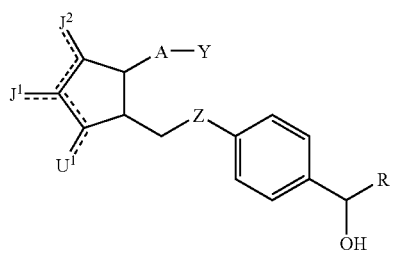

or a pharmaceutical salt thereof, or a prodrug thereof, wherein R is hydrogen or $C_{1-10}$ hydrocarbyl.

Another embodiment is a compound according to the structure

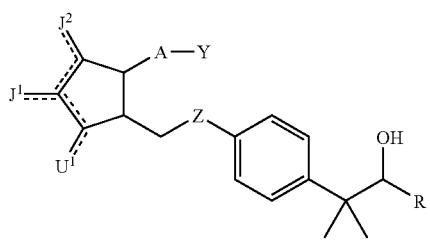

"C1-10" hydrocarbyl is hydrocarbyl having 1, 2, 3, 4, 5, 6, 7, 8, 9, or 10 carbon atoms.

Hydrocarbyl is a moiety consisting of only carbon and hydrogen, and includes, but is not limited to alkyl, alkenyl, alkynyl, and the like, and in some cases aryl, and combinations thereof.

Alkyl is hydrocarbyl having no double or triple bonds including:

linear alkyl such as methyl, ethyl, propyl, n-butyl, n-pentyl, n-hexyl, and the like;

branched alkyl such as isopropyl, branched butyl isomers (i.e. sec-butyl, tert-butyl, etc), branched pentyl isomers (i.e. isopentyl, etc), branched hexyl isomers, and higher branched alkyl fragments;

cycloalkyl such as cyclopropyl, cyclobutyl, cyclopentyl, cyclohexyl, cycloheptyl, etc.; and alkyl fragments consisting of both cyclic and noncyclic components, whether linear or branched, which may be attached to the remainder of the molecule at any available position including terminal, internal, or ring carbon atoms.

Alkenyl is hydrocarbyl having one or more double bonds including linear alkenyl, branched alkenyl, cyclic alkenyl, and combinations thereof in analogy to alkyl.

Alkynyl is hydrocarbyl having one or more triple bonds including linear alkynyl, branched alkynyl, cyclic alkynyl and combinations thereof in analogy to alkyl.

Aryl is an unsubstituted or substituted aromatic ring or ring system such as phenyl, naphthyl, biphenyl, and the like. Aryl may or may not be hydrocarbyl, depending upon whether it has substituents with heteroatoms.

Arylalkyl is alkyl which is substituted with aryl. In other words alkyl connects aryl to the remaining part of the molecule.

Examples are —$CH_2$-Phenyl, —$CH_2$—$CH_2$-Phenyl, and the like. Arylalkyl may or may not be hydrocarbyl, depending upon whether the aryl portion has substituents with heteroatoms.

Unconjugated dienes or polyenes have one or more double bonds which are not conjugated. They may be linear, branched, or cyclic, or a combination thereof.

Combinations of the above are also possible.

$C_{1-3}$ alkyl is alkyl having 1, 2, or 3 carbon atoms.

$C_{1-3}$ alkoxy is —O-alkyl having 1, 2, or 3 carbon atoms.

In another embodiment, B is substituted or unsubstituted phenyl.

In another embodiment, B is substituted or unsubstituted thienyl.

In another embodiment, B is substituted or unsubstituted naphthyl.

In another embodiment, B is substituted or unsubstituted furyl.

In another embodiment, B is substituted or unsubstituted pyridinyl.

In another embodiment, B is substituted or unsubstituted benzothienyl.

In another embodiment, B is substituted or unsubstituted indanyl.

In another embodiment, B is substituted or unsubstituted tetralonyl.

In another embodiment, B has 1, 2, 3, 4, or 5 substituents, wherein each substituent has one or more carbon, fluorine, chlorine, bromine, oxygen, sulfur, or atoms; and wherein all substituents taken together consist of 0, 1, 2, 3, 4, 5, 6, 7, 8, 9 or 10 carbon atoms; 0, 1, 2, 3, 4, 5, 6, 7, 8 or 9 fluorine atoms; 0, 1, 2 or 3 chlorine atoms, 0, 1, 2 or 3 bromine atoms, 0, 1, 2 or 3 oxygen atoms; 0, 1, 2, or 3 sulfur atoms; 0, 1, 2, or 3 nitrogen atoms.

In another embodiment, B has 1, 2, 3, 4, or 5 substituents, wherein each substituent has one or more carbon, fluorine, chlorine, bromine, or oxygen atoms; and wherein all substituents taken together consist of 0, 1, 2, 3, 4, 5, 6, 7, 8, 9 or 10 carbon atoms; 0, 1, 2, 3, 4, 5, 6, 7, 8 or 9 fluorine atoms; 0, 1, 2 or 3 chlorine atoms, 0, 1, 2 or 3 bromine atoms, and 0, 1, 2 or 3 oxygen atoms.

In another embodiment, B has a substituent of the formula $C_aH_bO_c$; wherein a is 0, 1, 2, 3, 4, 5, 6, 7, 8 or 9, b is 0, 1, 2, 3, 4, 5, 6, 7, 8, 9, 10, 11, 12, 13, 14, 15, 16, 17, 18 or 19; and c is 0, 1, 2, or 3.

In another embodiment, B has 1, 2, 3, or 4 alkyl substituents having 1, 2, 3, 4, 5, 6, 7, 8, 9 or 10 carbon atoms.

In another embodiment, B has a hydroxyalkyl substituent having 0, 1, 2, 3, 4, 5, 6, 7, 8, 9 or 10 carbon atoms and 1 or 2 hydroxy moieties.

In another embodiment, B has an alkyl substituent having 0, 1, 2, 3, 4, 5, 6, 7, 8, 9 or 10 carbon atoms.

In another embodiment, B has 1, 2, 3, or 4 halogen substituents.

In another embodiment, B has 1, 2, 3, or 4 chloro substituents.

In another embodiment, B has 1 chloro substituent.

In another embodiment, B has 2 chloro substituents.

In another embodiment, B has 1, 2, 3, or 4 trifluoromethyl substituents.

In another embodiment, B has 1, 2, or 3 trifluoromethyl substituents.

In another embodiment, B has 1 trifluoromethyl substituent.

In another embodiment, B has 2 trifluoromethyl substituents.

In another embodiment, B has a hydroxyl substituent.

Examples of useful moieties for B are depicted below. Each is individually contemplated as an embodiment.

Structure:

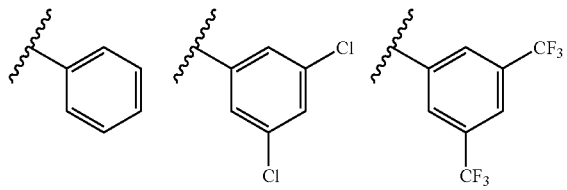

Name: unsubstituted phenyl | 3,5-dichlorophenyl | 3,5-di(trifluoromethyl)phenyl

Structure:

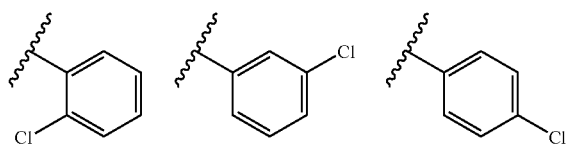

Name: 2-chlorophenyl | 3-chlorophenyl | 4-chlorophenyl

Structure:

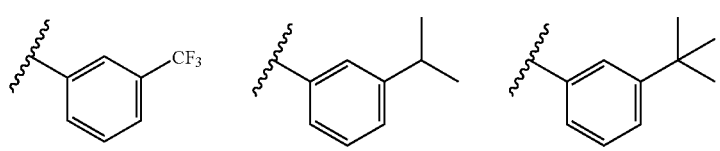

Name: 3-(trifluoromethyl)phenyl | 3-isopropylphenyl | 3-tert-butylphenyl

Structure:

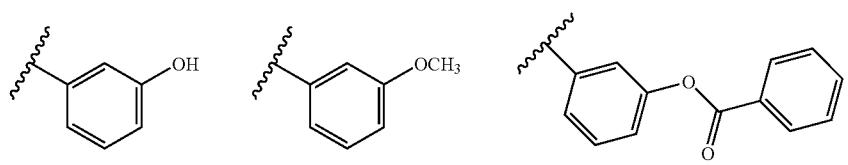

Name: 3-hydroxyphenyl | 3-methoxyphenyl | 3-(benzoyloxy)phenyl

-continued

Structure:

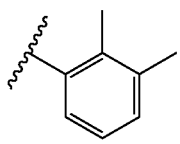 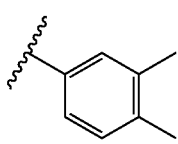 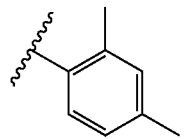

Name: 2,3-dimethylphenyl     3,4-dimethylphenyl     2,4-dimethylphenyl

Structure:

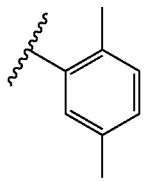 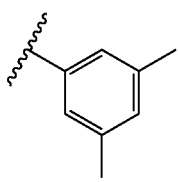 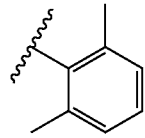

Name: 2,5-dimethylphenyl     3,5-dimethylphenyl     2,6-dimethylphenyl

Structure:

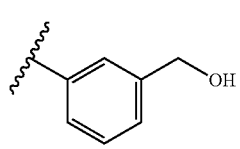 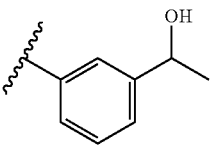 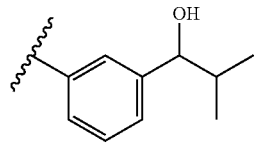

Name: 3-(hydroxymethyl)phenyl     3-(1-hydroxyethyl)phenyl     3-(1-hydroxy-2-methylpropyl)phenyl Structure:

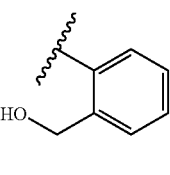 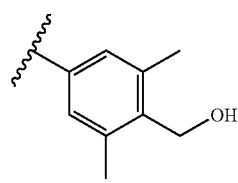 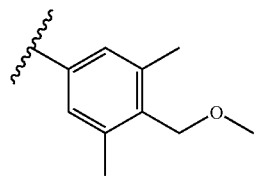

Name: 2-(hydroxymethyl)phenyl     4-(hydroxymethyl)-3,5-dimethylphenyl     4-(methoxymethyl)-3,5-dimethylphenyl Structure:

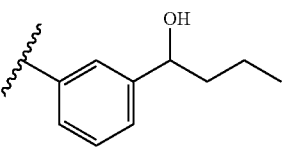 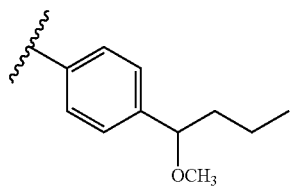 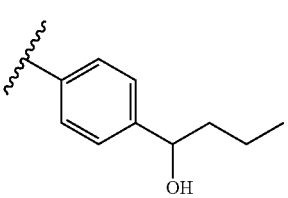

Name: 3-(1-hydroxybutyl)phenyl     4-(1-methoxybutyl)phenyl     4-(1-hydroxybutyl)phenyl -continued Structure:

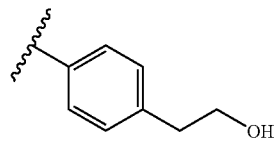 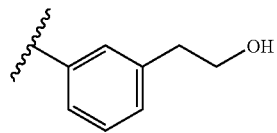 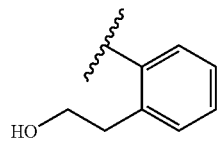

Name: 4-(2-hydroxyethyl)phenyl     3-(2-hydroxyethyl)phenyl     2-(2-hydroxyethyl)phenyl Structure:

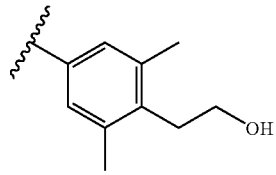 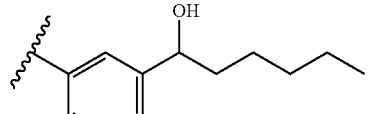 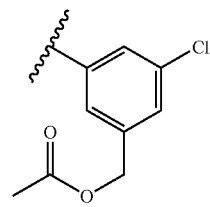

Name: 4-(2-hydroxyethyl)-3,5-dimethylphenyl     3-(1-hydroxyhexyl)phenyl     3-(acetoxymethyl)-5-chlorophenyl Structure:

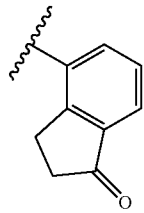 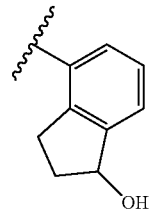 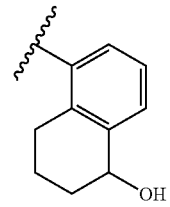

Name: 1-oxo-2,3-dihydro-1H-inden-4-yl     1-hydroxy-2,3-dihydro-1H-inden-4-yl     5-hydroxy-5,6,7,8-tetrahydronaphthalen-1-yl Structure:

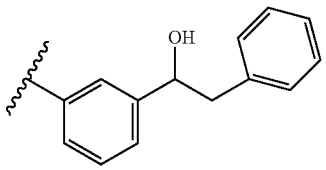 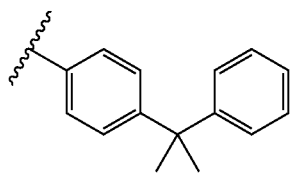

Name: 3-(1-hydroxy-2-phenylethyl)phenyl     4-(2-phenylpropan-2-yl)phenyl

Structure:

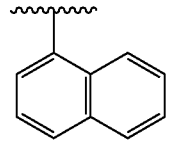 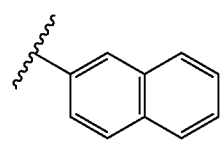

Name: naphthalen-1-yl     naphthalen-2-yl

Structure:

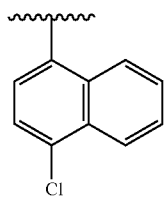

Name: 4-chloronaphthalen-1-yl

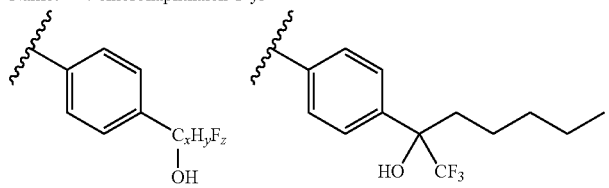

In the above embodiments, x is 5, 6, or 7, and y+z is 2x+1.
In one embodiment, x is 5 and y+z is 11.
In another embodiment, x is 6 and y+z is 13.
In another embodiment, x is 7 and y+z is 15.
In one embodiment, said compound is not

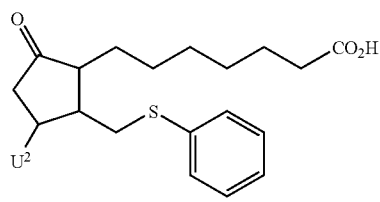

wherein $U^2$ is OH or H.

In another embodiment, said compound is not

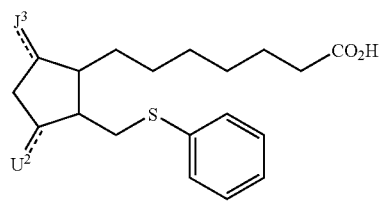

wherein $J^3$ is O or OH and $U^2$ is OH or H.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds may be in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

For treatment of diseases affecting the eye including glaucoma, these compounds can be administered topically, periocularly, intraocularly, or by any other effective means known in the art.

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer."

COMPOUND EXAMPLES

The following are hypothetical examples of useful compounds:

Compound Example 1

A compound of the formula

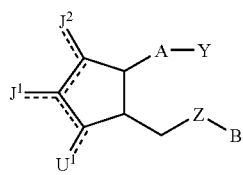

or a pharmaceutically acceptable salt thereof, or a prodrug thereof;

wherein a dashed line represents the presence or absence of a bond;

Y is an organic acid functional group, or an amide or ester thereof comprising up to 14 carbon atoms; or Y is hydroxymethyl or an ether thereof comprising up to 14 carbon atoms; or Y is a tetrazolyl functional group;

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced by S or O; or A is —(CH$_2$)$_m$—Ar—(CH$_2$)$_o$— wherein Ar is interarylene or heterointerarylene, the sum of m and o is 1, 2, 3, or 4, and wherein one CH$_2$ may be replaced by S or O;

U$^1$ is independently hydrogen; OH; O; S; F; Cl; Br; I; CN; or O-alkyl having 1, 2, 3, 4, 5 or 6 carbon atoms;

J$^1$ and J$^2$ are independently hydrogen; F; Cl; Br; I; O; OH; CN; O-alkyl having 1, 2, 3, 4, 5 or 6 carbon atoms; alkyl having 1, 2, 3, 4, 5, or 6 carbon atoms; or CF$_3$;

Z is S, SO, SO$_2$, NR, NCOR, or NSO$_2$R, wherein R is H or C$_{1-6}$ hydrocarbyl, and B is aryl or heteroaryl;

wherein said compound is not

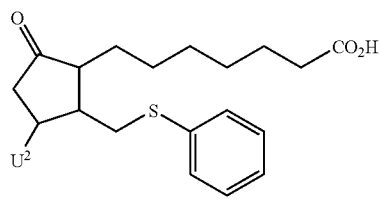

wherein U$^2$ is OH or H.

Compound Example 2

A compound which is a carboxylic acid or a bioisostere thereof, said carboxylic acid having a structure

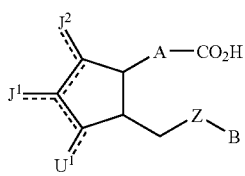

or a pharmaceutically acceptable salt thereof, or a prodrug thereof;

wherein a dashed line represents the presence or absence of a bond;

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced by S or O; or A is —(CH$_2$)$_m$—Ar—(CH$_2$)$_o$— wherein Ar is interarylene or heterointerarylene, the sum of m and o is 1, 2, 3, or 4, and wherein one CH$_2$ may be replaced by S or O;

U$^1$ is independently hydrogen; OH; O; S; F; Cl; Br; I; CN; or O-alkyl having 1, 2, 3, 4, 5 or 6 carbon atoms;

J$^1$ and J$^2$ are independently hydrogen; F; Cl; Br; I; O; OH; CN; O-alkyl having 1, 2, 3, 4, 5 or 6 carbon atoms; alkyl having 1, 2, 3, 4, 5, or 6 carbon atoms; or CF$_3$;

Z is S, SO, SO$_2$, NR, NCOR, or NSO$_2$R, wherein R is H or C$_{1-6}$ hydrocarbyl, and B is aryl or heteroaryl.

Compound Example 3

The compound according to compound example 1 wherein Y is selected from CO$_2$R$^2$, CON(R$^2$)$_2$, CON(OR$^2$)R$^2$, CON(CH$_2$CH$_2$OH)$_2$, CONH(CH$_2$CH$_2$OH), CH$_2$OH, P(O)(OH)$_2$, CONHSO$_2$R$^2$, SO$_2$N(R$^2$)$_2$, SO$_2$NHR$^2$,

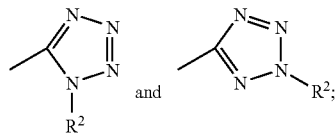

wherein R$^2$ is independently H, C$_1$-C$_6$ alkyl, unsubstituted phenyl, or unsubstituted biphenyl.

Compound Example 4

The compound according to compound example 1 or 3 of the formula

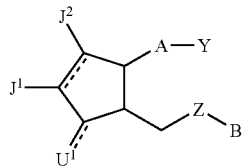

or a pharmaceutically acceptable salt thereof, or a prodrug thereof.

Compound Example 5

The compound according to compound example 1 or 3 having the formula

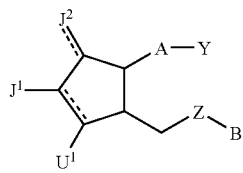

or a pharmaceutically acceptable salt thereof, or a prodrug thereof.

Compound Example 6

The compound according to compound example 1 or 3 having the formula

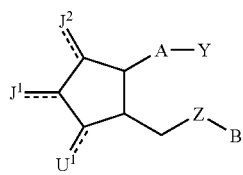

or a pharmaceutically acceptable salt thereof, or a prodrug thereof.

Compound Example 7

The compound according to any one of compound examples 1 to 6 wherein A is (3-methylphenoxy)methyl.

Compound Example 8

The compound according to any one of compound examples 1 to 6 wherein A is (4-but-2-ynyloxy)methyl.

Compound Example 9

The compound according to any one of compound examples 1 to 6 wherein A is 2-(2-ethylthio)thiazol-4-yl.

Compound Example 10

The compound according to any one of compound examples 1 to 6 wherein A is 2-(3-propyl)thiazol-5-yl.

Compound Example 11

The compound according to any one of compound examples 1 to 6 wherein A is 3-(methoxymethyl)phenyl.

Compound Example 12

The compound according to any one of compound examples 1 to 6 wherein A is 3-(3-propyl)phenyl.

Compound Example 13

The compound according to any one of compound examples 1 to 6 wherein A is 3-methylphenethyl.

Compound Example 14

The compound according to any one of compound examples 1 to 6 wherein A is 4-(2-ethyl)phenyl.

Compound Example 15

The compound according to any one of compound examples 1 to 6 wherein A is 4-phenethyl.

Compound Example 16

The compound according to any one of compound examples 1 to 6 wherein A is 4-methoxybutyl.

Compound Example 17

The compound according to any one of compound examples 1 to 6 wherein A is 5-(methoxymethyl)furan-2-yl.

Compound Example 18

The compound according to any one of compound examples 1 to 6 wherein A is 5-(methoxymethyl)thiophen-2-yl.

Compound Example 19

The compound according to any one of compound examples 1 to 6 wherein A is 5-(3-propyl)furan-2-yl.

Compound Example 20

The compound according to any one of compound examples 1 to 6 wherein A is 5-(3-propyl)thiophen-2-yl.

Compound Example 21

The compound according to any one of compound examples 1 to 6 wherein A is 6-hexyl.

Compound Example 22

The compound according to any one of compound examples 1 to 6 wherein A is (Z)-6-hex-4-enyl.

Compound Example 23

The compound according to any one of compound examples 1, 3, 4 and 7 to 22 having the formula

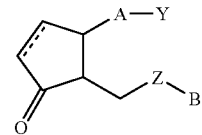

or a pharmaceutically acceptable salt thereof or a prodrug thereof.

Compound Example 24

The compound according to any one of compound examples 1, 3, and 7 to 22 having the formula

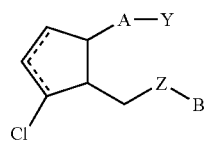

or a pharmaceutically acceptable salt thereof or a prodrug thereof.

Compound Example 25

The compound according to any one of compound examples 1, 3, and 6 to 22 having the formula

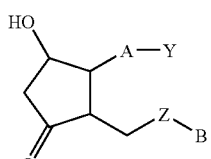

or a pharmaceutically acceptable salt thereof or a prodrug thereof.

Compound Example 26

The compound according to any one of compound examples 1, 3, and 6 to 22 having the formula

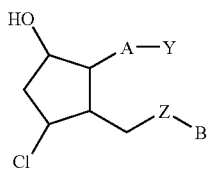

or a pharmaceutically acceptable salt thereof or a prodrug thereof.

Compound Example 27

The compound according to any one of compound examples 1, 3, and 6 to 22 having the formula

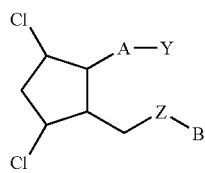

or a pharmaceutically acceptable salt thereof or a prodrug thereof.

Compound Example 28

The compound according to any one of compound examples 1, 3, and 6 to 22 having the formula

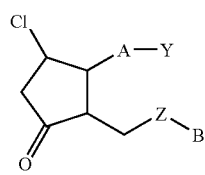

or a pharmaceutically acceptable salt thereof or a prodrug thereof.

Compound Example 29

The compound according to any one of compound examples 1, 3, and 6 to 22 having the formula

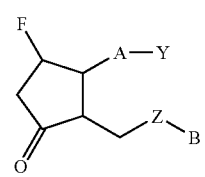

or a pharmaceutically acceptable salt thereof or a prodrug thereof.

Compound Example 30

The compound according to any one of compound examples 1, 3, and 6 to 22 having the formula

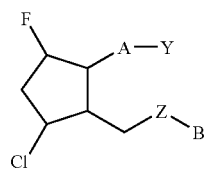

or a pharmaceutically acceptable salt thereof or a prodrug thereof.

Compound Example 31

The compound according to any one of compound examples 1 to 3, and 7 to 22 wherein $U^1$ is O.

Compound Example 32

The compound according to any one of compound examples 1 to 3, and 7 to 22 wherein $U^1$ is S.

Compound Example 33

The compound according to any one of compound examples 1 to 3, and 7 to 22 wherein $U^1$ is F.

Compound Example 34

The compound according to any one of compound examples 1 to 3, and 7 to 22 wherein $U^1$ is Cl.

Compound Example 35

The compound according to any one of compound examples 1 to 3, and 7 to 22 wherein $U^1$ is Br.

Compound Example 36

The compound according to any one of compound examples 1 to 3, and 7 to 22 wherein $U^1$ is I.

Compound Example 37

The compound according to any one of compound examples 1 to 3, and 7 to 22 wherein $U^1$ is CN.

Compound Example 38

The compound according to any one of compound examples 1 to 3, and 7 to 22 wherein $U^1$ is O-alkyl having 1, 2, 3, 4, 5 or 6 carbon atoms.

Compound Example 39

The compound according to any one of compound examples 1 to 3, 7 to 22, and 31 to 38, wherein $J^1$ is hydrogen.

Compound Example 40

The compound according to any one of compound examples 1 to 3, 7 to 22, and 31 to 38, wherein $J^1$ is F.

Compound Example 41

The compound according to any one of compound examples 1 to 3, 7 to 22, and 31 to 38, wherein $J^1$ is Cl.

Compound Example 42

The compound according to any one of compound examples 1 to 3, 7 to 22, and 31 to 38, wherein $J^1$ is Br.

Compound Example 43

The compound according to any one of compound examples 1 to 3, 7 to 22, and 31 to 38, wherein $J^1$ is I.

Compound Example 44

The compound according to any one of compound examples 1 to 3, 7 to 22, and 31 to 38, wherein $J^1$ is O.

Compound Example 45

The compound according to any one of compound examples 1 to 3, 7 to 22, and 31 to 38, wherein $J^1$ is OH.

Compound Example 46

The compound according to any one of compound examples 1 to 3, 7 to 22, and 31 to 38, wherein $J^1$ is CN.

Compound Example 47

The compound according to any one of compound examples 1 to 3, 7 to 22, and 31 to 38, wherein $J^1$ is O-alkyl having 1, 2, 3, 4, 5 or 6 carbon atoms.

Compound Example 48

The compound according to any one of compound examples 1 to 3, 7 to 22, and 31 to 38, wherein $J^1$ is alkyl having 1, 2, 3, 4, 5, or 6 carbon atoms.

Compound Example 49

The compound according to any one of compound examples 1 to 3, 7 to 22, and 31 to 38, wherein $J^1$ is $CF_3$.

Compound Example 50

The compound according to any one of compound examples 1 to 3, 7 to 22, and 31 to 49 wherein $J^2$ is hydrogen.

Compound Example 51

The compound according to any one of compound examples 1 to 3, 7 to 22, and 31 to 49 wherein $J^2$ is F.

Compound Example 52

The compound according to any one of compound examples 1 to 3, 7 to 22, and 31 to 49 wherein $J^2$ is Cl.

Compound Example 53

The compound according to any one of compound examples 1 to 3, 7 to 22, and 31 to 49 wherein $J^2$ is Br.

Compound Example 54

The compound according to any one of compound examples 1 to 3, 7 to 22, and 31 to 49 wherein $J^2$ is I.

Compound Example 55

The compound according to any one of compound examples 1 to 3, 7 to 22, and 31 to 49 wherein $J^2$ is O.

Compound Example 56

The compound according to any one of compound examples 1 to 3, 7 to 22, and 31 to 49 wherein $J^2$ is OH.

Compound Example 57

The compound according to any one of compound examples 1 to 3, 7 to 22, and 31 to 49 wherein $J^2$ is CN.

Compound Example 58

The compound according to any one of compound examples 1 to 3, 7 to 22, and 31 to 49 wherein $J^2$ is O-alkyl having 1, 2, 3, 4, 5 or 6 carbon atoms.

Compound Example 59

The compound according to any one of compound examples 1 to 3, 7 to 22, and 31 to 49 wherein $J^2$ is alkyl having 1, 2, 3, 4, 5, or 6 carbon atoms.

Compound Example 60

The compound according to any one of compound examples 1 to 3, 7 to 22, and 31 to 49 wherein $J^2$ is $CF_3$.

Compound Example 61

The compound according to any one of compound examples 1 to 60 wherein B is substituted or unsubstituted phenyl.

Compound Example 62

The compound according to any one of compound examples 1 to 60 wherein B is substituted or unsubstituted thienyl.

Compound Example 63

The compound according to any one of compound examples 1 to 60 wherein B is substituted or unsubstituted naphthyl.

Compound Example 64

The compound according to any one of compound examples 1 to 60 wherein B is substituted or unsubstituted furyl.

Compound Example 65

The compound according to any one of compound examples 1 to 60 wherein B is substituted or unsubstituted pyridinyl.

Compound Example 66

The compound according to any one of compound examples 1 to 60 wherein B is substituted or unsubstituted benzothienyl.

Compound Example 67

The compound according to any one of compound examples 1 to 60 wherein B is substituted or unsubstituted indanyl.

Compound Example 68

The compound according to any one of compound examples 1 to 60 wherein B is substituted or unsubstituted tetralonyl.

Compound Example 69

The compound according to any one of compound examples 1 to 60 wherein B has 1, 2, 3, 4, or 5 substituents, wherein each substituent has one or more carbon, fluorine, chlorine, bromine, or oxygen atoms; and wherein all substituents taken together consist of 0, 1, 2, 3, 4, 5, 6, 7, 8, 9 or 10 carbon atoms; 0, 1, 2, 3, 4, 5, 6, 7, 8 or 9 fluorine atoms; 0, 1, 2 or 3 chlorine atoms, 0, 1, 2 or 3 bromine atoms, and 0, 1, 2 or 3 oxygen atoms.

Compound Example 70

The compound according to any one of compound examples 1 to 60 wherein B has a substituent of the formula $C_aH_bO_c$; wherein a is 0, 1, 2, 3, 4, 5, 6, 7, 8 or 9, b is 0, 1, 2, 3, 4, 5, 6, 7, 8, 9, 10, 11, 12, 13, 14, 15, 16, 17, 18 or 19; and c is 0, 1, 2, or 3.

Compound Example 71

The compound according to any one of compound examples 1 to 60 wherein B has 1, 2, 3, or 4 alkyl substituents having 1, 2, 3, 4, 5, 6, 7, 8, 9 or 10 carbon atoms.

Compound Example 72

The compound according to any one of compound examples 1 to 60 wherein B has a hydroxyalkyl substituent having 0, 1, 2, 3, 4, 5, 6, 7, 8, 9 or 10 carbon atoms and 1 or 2 hydroxy moieties.

Compound Example 73

The compound according to any one of compound examples 1 to 60 wherein B has an alkyl substituent having 0, 1, 2, 3, 4, 5, 6, 7, 8, 9 or 10 carbon atoms.

Compound Example 74

The compound according to any one of compound examples 1 to 60 wherein B has 1, 2, 3, or 4 halogen substituents.

Compound Example 75

The compound according to any one of compound examples 1 to 60 wherein B has 1, 2, 3, or 4 chloro substituents.

Compound Example 76

The compound according to any one of compound examples 1 to 60 wherein B has 1 chloro substituent.

Compound Example 77

The compound according to any one of compound examples 1 to 60 wherein B has 2 chloro substituents.

Compound Example 78

The compound according to any one of compound examples 1 to 60 wherein B has 1, 2, 3, or 4 trifluoromethyl substituents.

Compound Example 79

The compound according to any one of compound examples 1 to 60 wherein B has 1, 2, or 3 trifluoromethyl substituents.

Compound Example 80

The compound according to any one of compound examples 1 to 60 wherein B has 1 trifluoromethyl substituent.

Compound Example 81

The compound according to any one of compound examples 1 to 60 wherein B has 2 trifluoromethyl substituents.

Compound Example 82

The compound according to any one of compound examples 1 to 60 wherein B has a hydroxyl substituent.

Compound Example 83

The compound according to any one of compound examples 1 to 61 wherein B is unsubstituted phenyl.

Compound Example 84

The compound according to any one of compound examples 1 to 61 wherein B is 3,5-dichlorophenyl.

Compound Example 85

The compound according to any one of compound examples 1 to 61 wherein B is 3,5-di(trifluoromethyl)phenyl.

Compound Example 86

The compound according to any one of compound examples 1 to 61 wherein B is 2-chlorophenyl.

Compound Example 87

The compound according to any one of compound examples 1 to 61 wherein B is 3-chlorophenyl.

Compound Example 88

The compound according to any one of compound examples 1 to 61 wherein B is 4-chlorophenyl.

Compound Example 89

The compound according to any one of compound examples 1 to 61 wherein B is 3-(trifluoromethyl)phenyl.

Compound Example 90

The compound according to any one of compound examples 1 to 61 wherein B is 3-isopropylphenyl.

Compound Example 91

The compound according to any one of compound examples 1 to 61 wherein B is 3-tert-butylphenyl.

Compound Example 92

The compound according to any one of compound examples 1 to 61 wherein B is 3-hydroxyphenyl.

Compound Example 93

The compound according to any one of compound examples 1 to 61 wherein B is 3-methoxyphenyl.

Compound Example 94

The compound according to any one of compound examples 1 to 61 wherein B is 3-(benzoyloxy)phenyl.

Compound Example 95

The compound according to any one of compound examples 1 to 61 wherein B is 2,3-dimethylphenyl.

Compound Example 96

The compound according to any one of compound examples 1 to 61 wherein B is 3,4-dimethylphenyl.

Compound Example 97

The compound according to any one of compound examples 1 to 61 wherein B is 2,4-dimethylphenyl.

Compound Example 98

The compound according to any one of compound examples 1 to 61 wherein B is 2,5-dimethylphenyl.

Compound Example 99

The compound according to any one of compound examples 1 to 61 wherein B is 3,5-dimethylphenyl.

Compound Example 100

The compound according to any one of compound examples 1 to 61 wherein B is 2,6-dimethylphenyl.

Compound Example 101

The compound according to any one of compound examples 1 to 61 wherein B is 3-(hydroxymethyl)phenyl.

Compound Example 102

The compound according to any one of compound examples 1 to 61 wherein B is 3-(1-hydroxyethyl)phenyl.

Compound Example 103

The compound according to any one of compound examples 1 to 61 wherein B is 3-(1-hydroxy-2-methylpropyl)phenyl.

Compound Example 104

The compound according to any one of compound examples 1 to 61 wherein B is 2-(hydroxymethyl)phenyl.

Compound Example 105

The compound according to any one of compound examples 1 to 61 wherein B is 4-(hydroxymethyl)-3,5-dimethylphenyl.

Compound Example 106

The compound according to any one of compound examples 1 to 61 wherein B is 4-(methoxymethyl)-3,5-dimethylphenyl.

Compound Example 107

The compound according to any one of compound examples 1 to 61 wherein B is 3-(1-hydroxybutyl)phenyl.

Compound Example 108

The compound according to any one of compound examples 1 to 61 wherein B is 4-(1-methoxybutyl)phenyl.

Compound Example 109

The compound according to any one of compound examples 1 to 61 wherein B is 4-(1-hydroxybutyl)phenyl.

Compound Example 110

The compound according to any one of compound examples 1 to 61 wherein B is 4-(2-hydroxyethyl)phenyl.

Compound Example 111

The compound according to any one of compound examples 1 to 61 wherein B is 3-(2-hydroxyethyl)phenyl.

Compound Example 112

The compound according to any one of compound examples 1 to 61 wherein B is 2-(2-hydroxyethyl)phenyl.

Compound Example 113

The compound according to any one of compound examples 1 to 61 wherein B is 4-(2-hydroxyethyl)-3,5-dimethylphenyl.

Compound Example 114

The compound according to any one of compound examples 1 to 61 wherein B is 3-(1-hydroxyhexyl)phenyl.

Compound Example 115

The compound according to any one of compound examples 1 to 61 wherein B is 3-(acetoxymethyl)-5-chlorophenyl.

Compound Example 116

The compound according to any one of compound examples 1 to 61 wherein B is 1-oxo-2,3-dihydro-1H-inden-4-yl.

Compound Example 117

The compound according to any one of compound examples 1 to 61 wherein B is 1-hydroxy-2,3-dihydro-1H-inden-4-yl.

Compound Example 118

The compound according to any one of compound examples 1 to 61 wherein B is 5-hydroxy-5,6,7,8-tetrahydronaphthalen-1-yl.

Compound Example 119

The compound according to any one of compound examples 1 to 61 wherein B is 3-(1-hydroxy-2-phenylethyl)phenyl.

Compound Example 120

The compound according to any one of compound examples 1 to 61 wherein B is 4-(2-phenylpropan-2-yl)phenyl.

Compound Example 121

The compound according to any one of compound examples 1 to 60 wherein B is naphthalen-2-yl.

Compound Example 122

The compound according to any one of compound examples 1 to 60 wherein B is naphthalen-1-yl.

Compound Example 123

The compound according to any one of compound examples 1 to 60 wherein B is 4-chloronaphthalen-1-yl.

Compound Example 124

The compound according to any one of compound examples 1 to 3, 7 to 22, and 39 to 123 wherein $U^1$ is hydrogen.

Compound Example 125

The compound according to any one of compound examples 1 to 3, 7 to 22, and 39 to 123 wherein $U^1$ is OH.

Compound Example 126

The compound according to compound example 1 or 2 wherein said compound is not

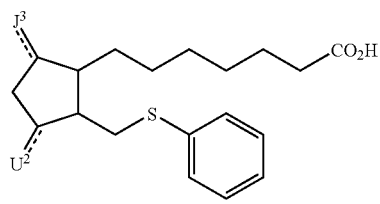

wherein $J^3$ is O or OH and $U^2$ is OH or H.

Compound Example 127

The compound according to any one of compound examples 1 to 125 wherein Z is S.

Compound Example 128

The compound according to any one of compound examples 1 to 125 wherein Z is NH.

Compound Example 129

The compound according to any one of compound examples 1 to 125 wherein Z is $NCH_3$.

Compound Example 130

The compound according to any one of compound examples 1 to 125 wherein Z is SO.

Compound Example 131

The compound according to any one of compound examples 1 to 125 wherein Z is $SO_2$.

Compound Example 132

The compound according to any one of compound examples 1 to 125 wherein Z is $NSO_2CH_3$.

Compound Example 133

The compound according to any one of compound examples 1 to 125 wherein Z is $NCOCH_3$.

Composition Example

A composition comprising a compound according to any one of compound examples 1 to 133, wherein said composition is a liquid which is ophthalmically acceptable.

Medicament Examples

Use of a compound according to any one of compound examples 1 to 133 in the manufacture of a medicament for the treatment of glaucoma or ocular hypertension in a mammal.

Use of a compound according to any one of compound examples 1 to 133 in the manufacture of a medicament for the treatment of baldness in a person.

A medicament comprising a compound according to any one of compound examples 1 to 133, wherein said composition is a liquid which is ophthalmically acceptable.

Method Example

A method comprising administering a compound according to any one of compound examples 1 to 133 to a mammal for the treatment of glaucoma or ocular hypertension.

Kit Example

A kit comprising a composition comprising compound according to any one of compound examples 1 to 133, a container, and instructions for administration of said composition to a mammal for the treatment of glaucoma or ocular hypertension.

"Treatment," "treat," or any other form of these words as used herein are intended to mean use in the diagnosis, cure, mitigation, treatment, or prevention of disease in man or other animals.

H1 through H72 are hypothetical examples of useful compounds.

H1
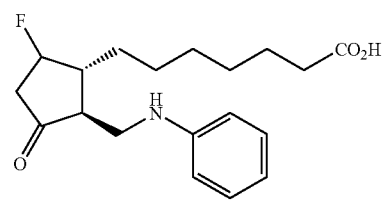

H2
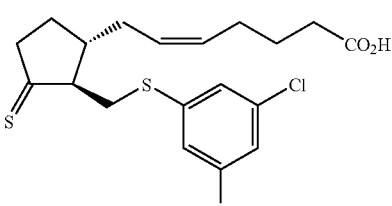

H3
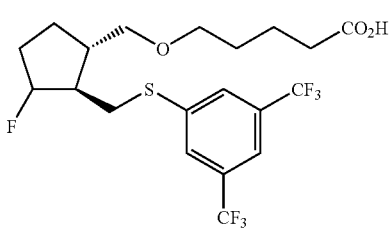

H4
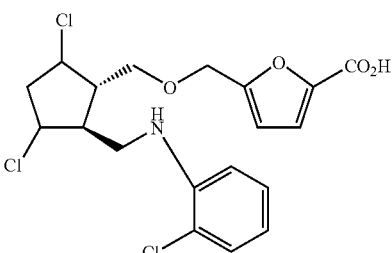

H5
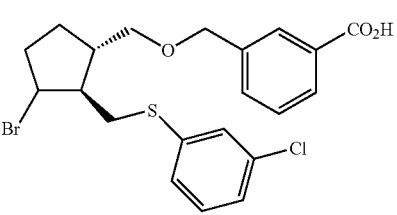

-continued

H6
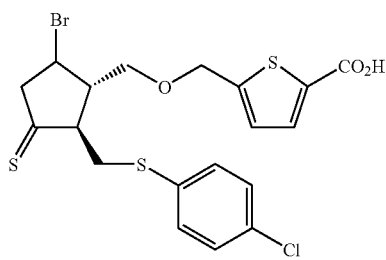

H7
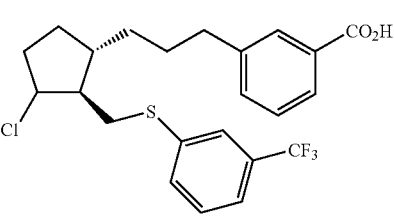

H8
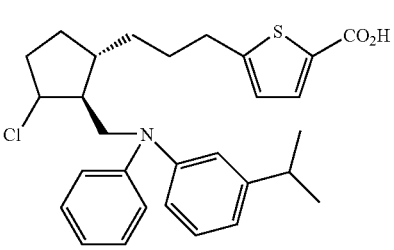

H9
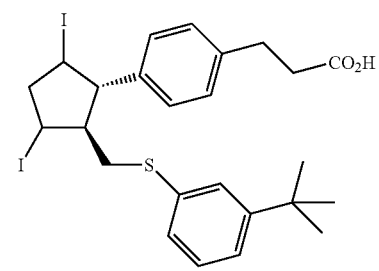

H10
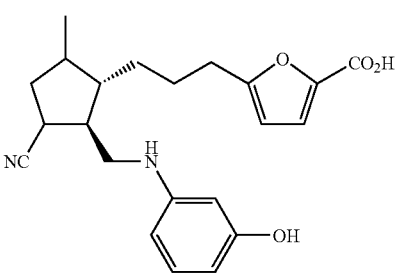

H11
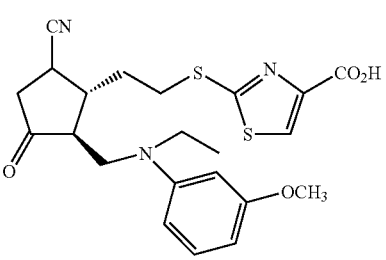

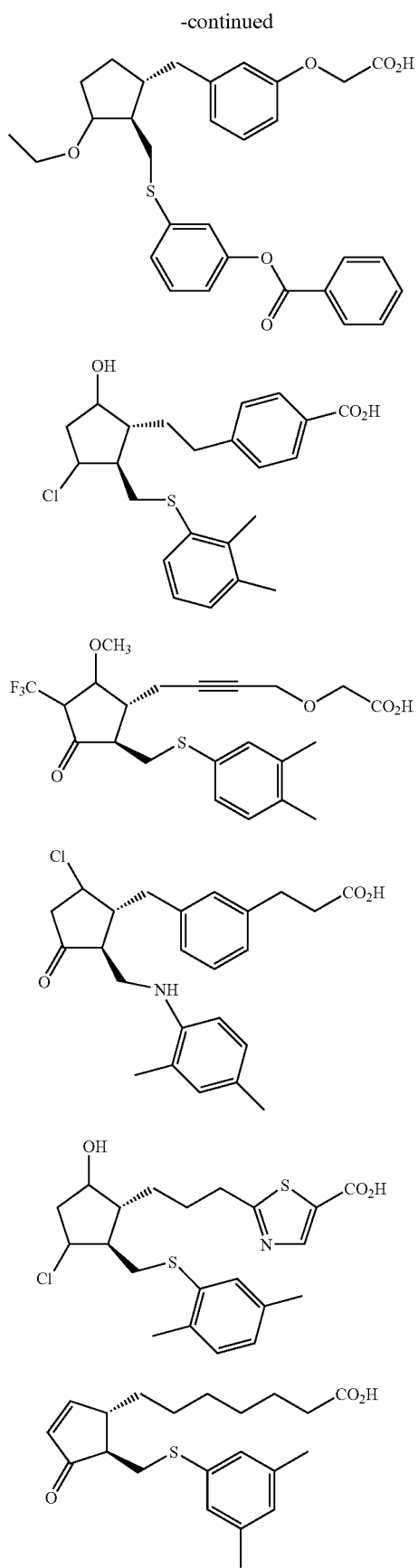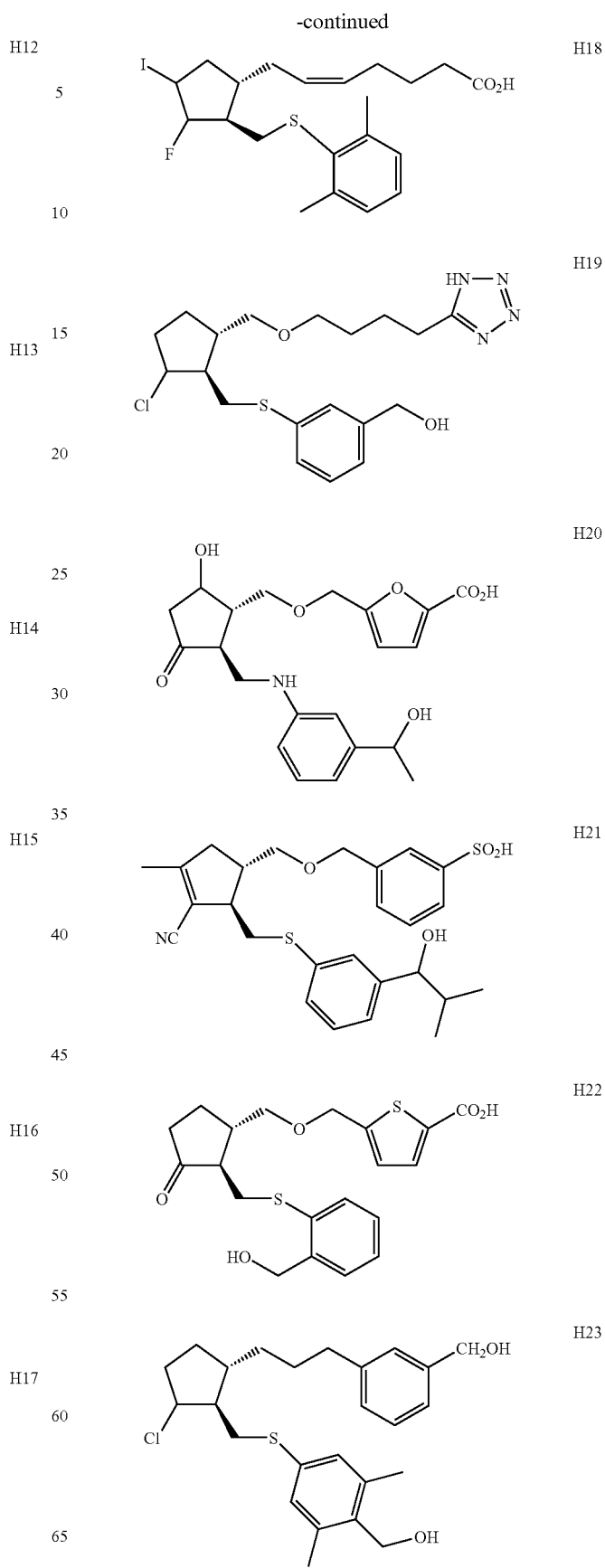

-continued
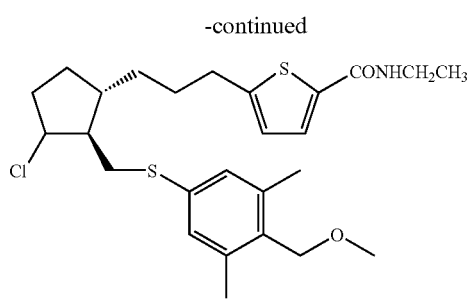
H24
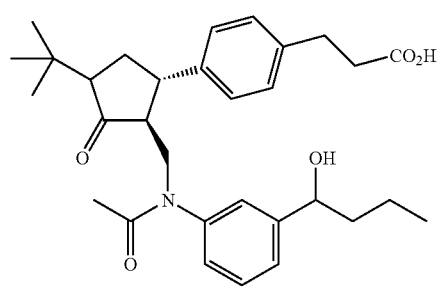
H25
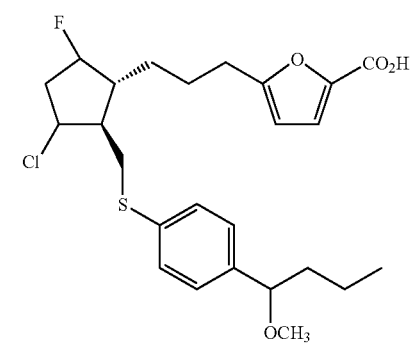
H26
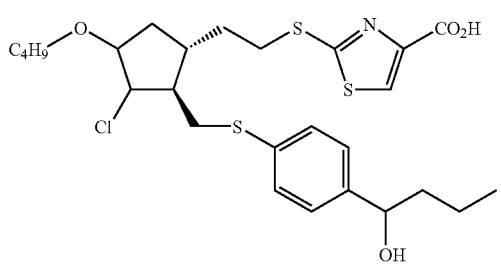
H27
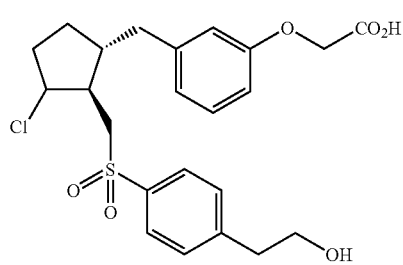
H28
-continued
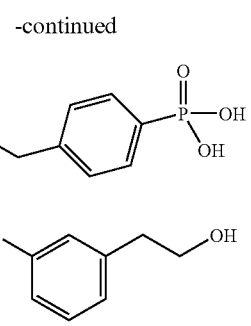
H29
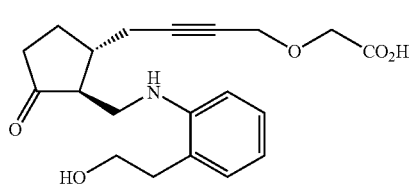
H30
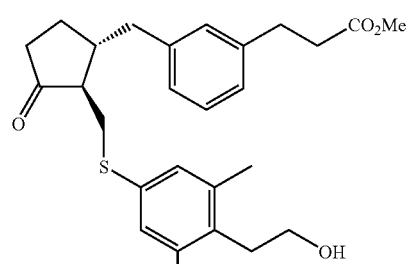
H31
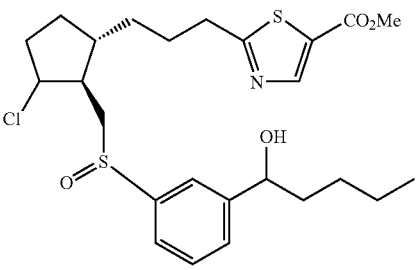
H32
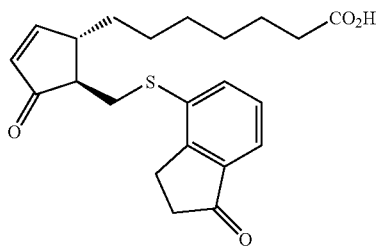
H33
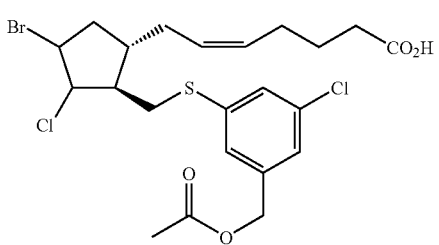
H34

-continued
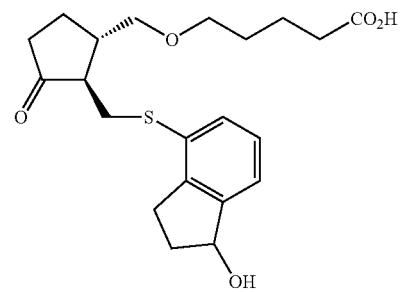 H35
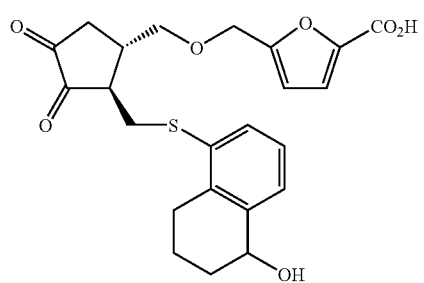 H36
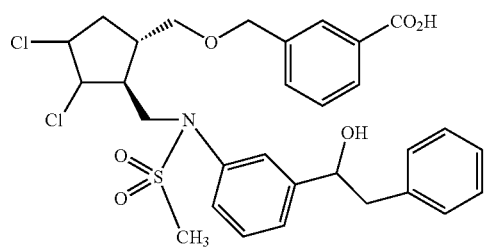 H37
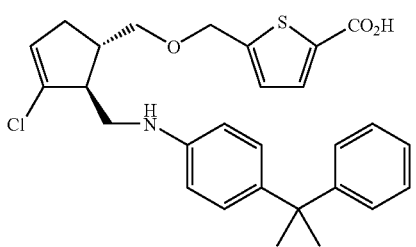 H38
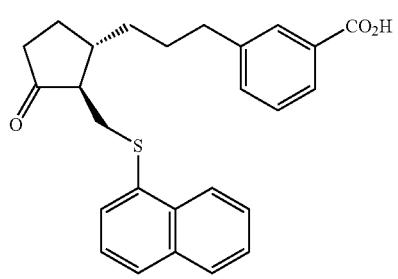 H39
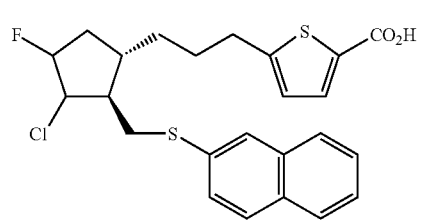 H40
-continued
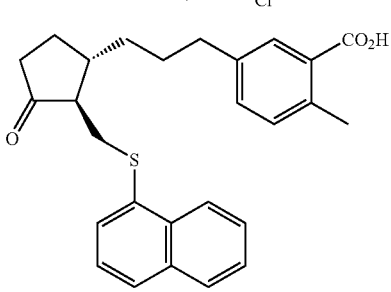 H41
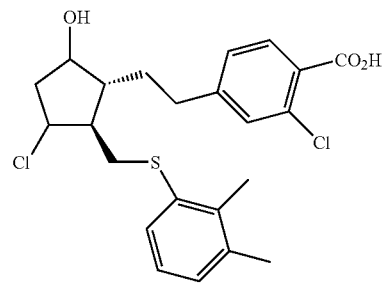 H42
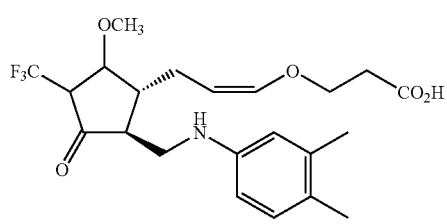 H43
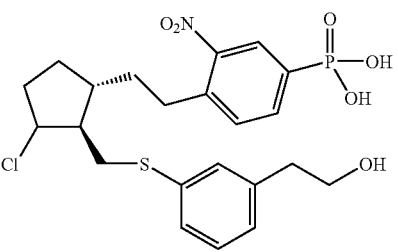 H44
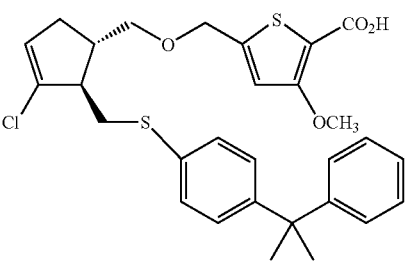 H45
H46

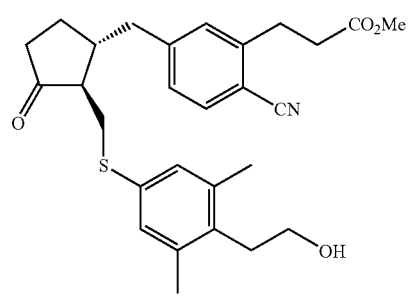
H47
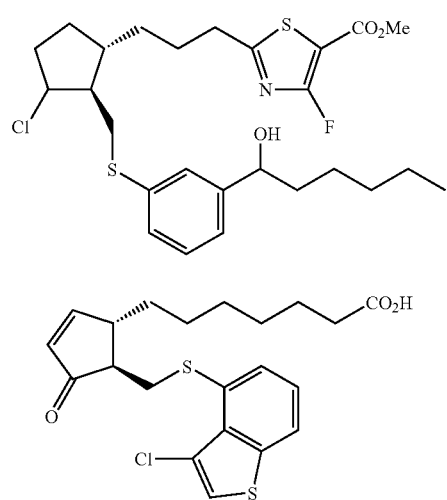
H48
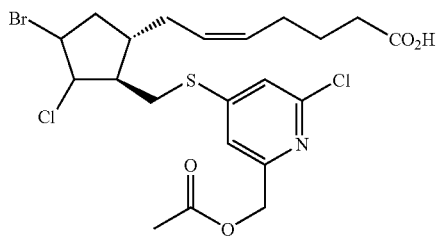
H49
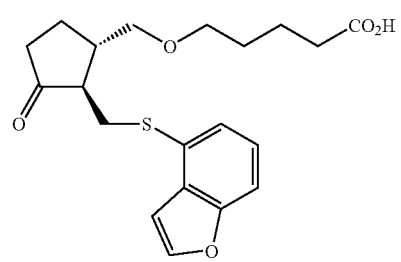
H50
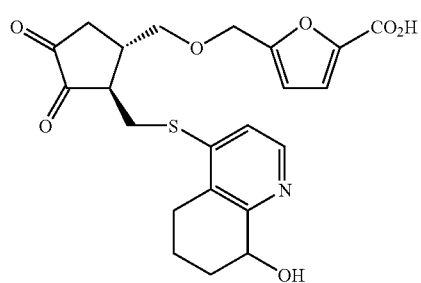
H51
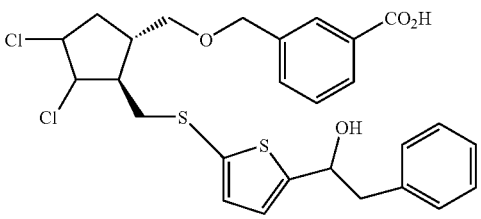
H53
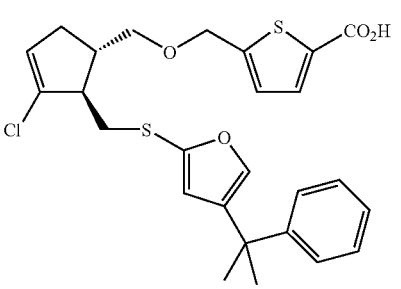
H54
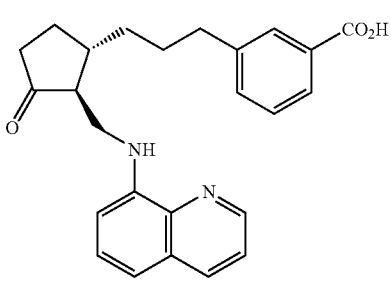
H55
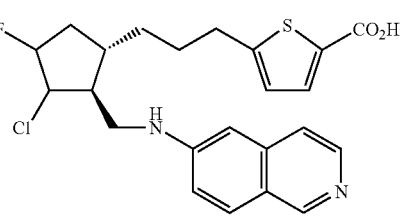
H56
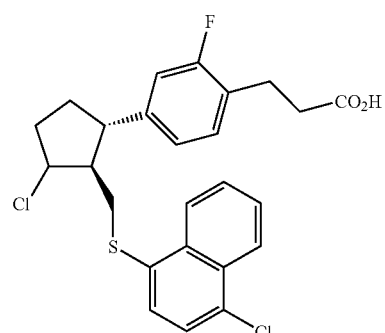
H57
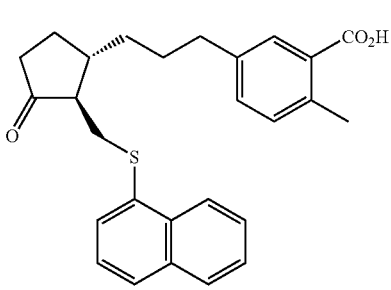
H58

-continued
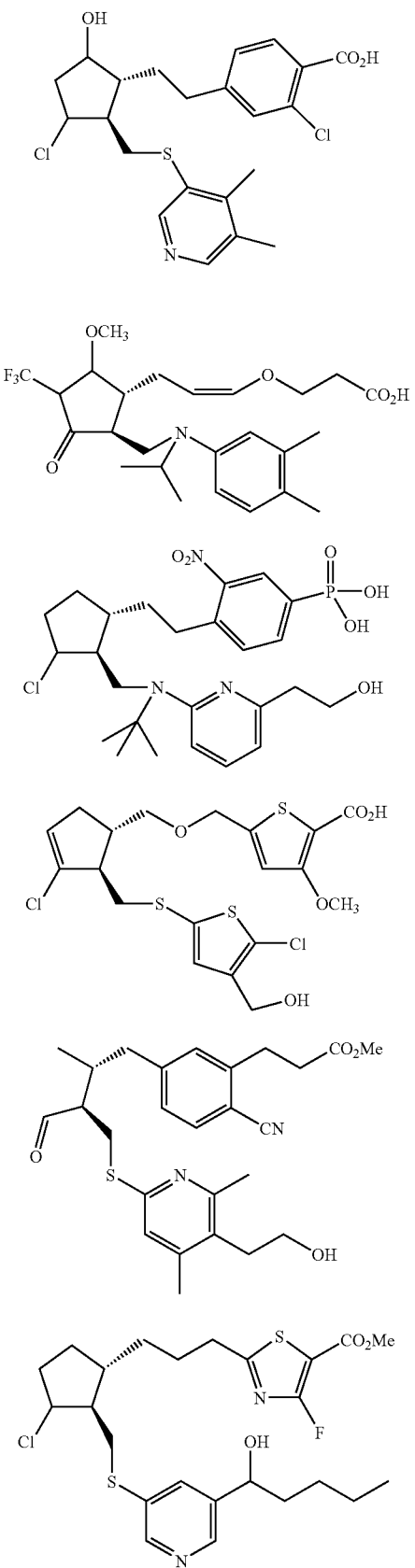
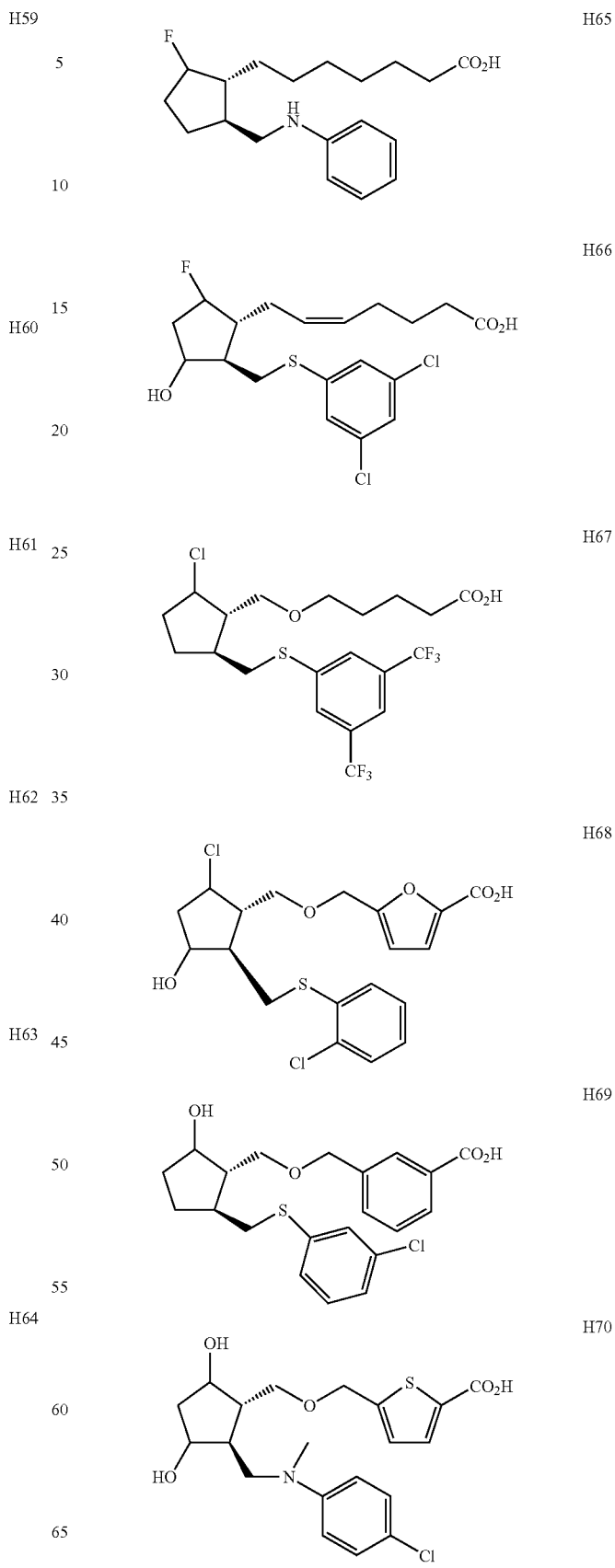

-continued

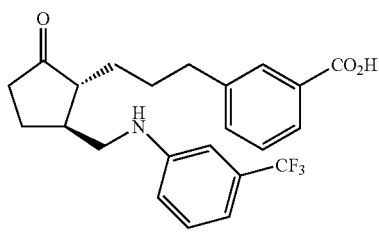

H71

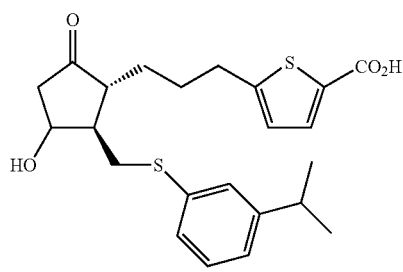

H72

Synthetic Example 1

(Z)-7-[(1R,2R,3R,5R)-5-Chloro-2-(3,5-dichloro-phenylsulfanylmethyl)-3-hydroxy-cyclopentyl]-hept-5-enoic acid (5)

Step 1. Mesylation of 1 to Give 2

Triethylamine (26 μL, 0.19 mmol) and methanesulfonyl chloride (12 μL, 0.15 mmol) were added sequentially to a solution of (Z)-7-[(1R,2S,3R,5R)-5-chloro-2-hydroxymethyl-3-(tetrahydro-pyran-2-yloxy)-cyclopentyl]-hept-5-enoic acid allyl ester (1, see U.S. Provisional Patent Application No. 60/757,696, filed Jan. 10, 2006, which is incorporated by reference herein; 50 mg, 0.125 mmol) in $CH_2Cl_2$ (1.25 mL) at 0° C. The reaction mixture was allowed to warm to room temperature. After 3 d at room temperature, the reaction mixture was partitioned between saturated aqueous $NaHCO_3$ (5 mL) and $CH_2Cl_2$ (5 mL). The phases were separated and the aqueous phase was extracted with $CH_2Cl_2$ (2×5 mL). The combined extracts were washed with brine (5 mL), dried ($MgSO_4$), filtered and concentrated in vacuo to afford crude mesylate 2 which was used without further purification.

Step 2. Reaction of 2 to Give Thiol 3

A solution of 3,5-dichlorobenzenethiol (78 mg, 0.44 mmol) in DMF (3 mL) was added to a suspension of sodium hydride (60 wt % in oil, 17 mg, 0.43 mmol) in DMF (1 mL) at room temperature. After 30 min at room temperature, a solution of mesylate 2 (crude, ~0.125 mmol) in THF (1.2 mL) was added. After 1 h, the reaction mixture was heated at 35° C. After 18 h at 35° C., the reaction mixture was partitioned between aqueous HCl (0.1 N, 20 mL) and EtOAc (20 mL). The phases were separated and the organic phase was washed with $H_2O$ (15 mL) and brine (15 mL), dried ($MgSO_4$), filtered and concentrated in vacuo. Purification of the crude residue by flash column chromatography on 40 g of silica gel (100% hexane→100% EtOAc, gradient) afforded 20 mg (29% over two steps) of thiol 3.

Step 3. Deprotection of 3 to Give 4

Pyridinium p-toluenesulfonate (PPTs, 1 mg, 0.004 mmol) was added to a solution of 3 (20 mg, 0.035 mmol) in methanol (0.35 mL) at room temperature under nitrogen. The solution was heated at 40° C. overnight, then cooled and concentrated in vacuo. Purification of the crude residue by flash column chromatography on 4 g of silica gel (100% hexane→100% EtOAc, gradient) afforded 11 mg (65%) of alcohol 4.

Step 4. Saponification of 4 to Give 5

Lithium hydroxide (92 μL of a 1.0 M aqueous solution, 0.092 mmol) was added to a solution of ester 4 (11 mg, 0.023 mmol) in THF (0.1 mL). After stirring overnight at room temperature, the reaction mixture was partitioned between aqueous HCl (0.1 N, 5 mL) and EtOAc (5 mL). The phases were separated and the aqueous phase was extracted with EtOAc (2×5 mL). The combined extracts were dried ($MgSO_4$), filtered and concentrated in vacuo to afford 8 mg (79%) of the title compound (5).

Synthetic Methods

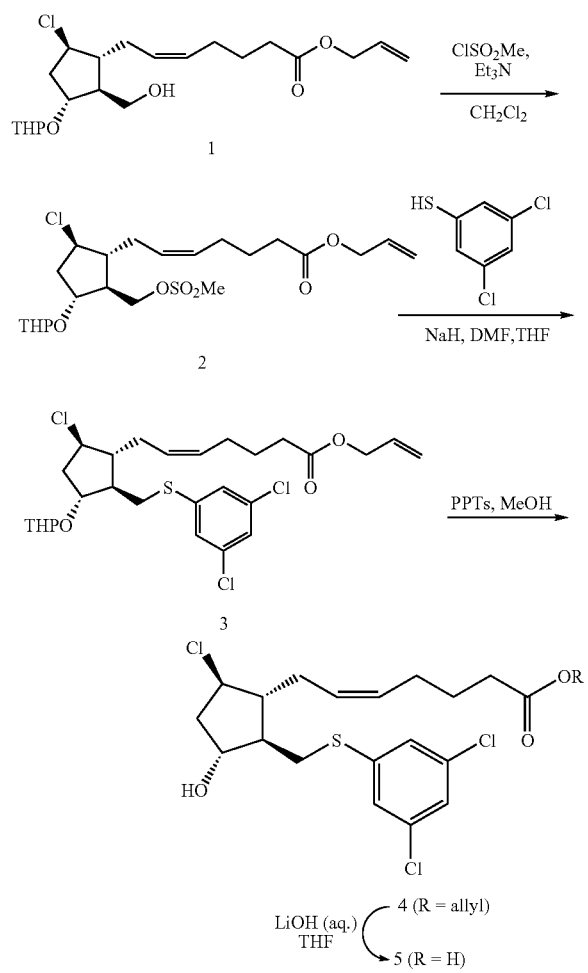

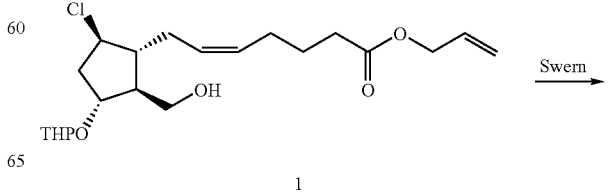

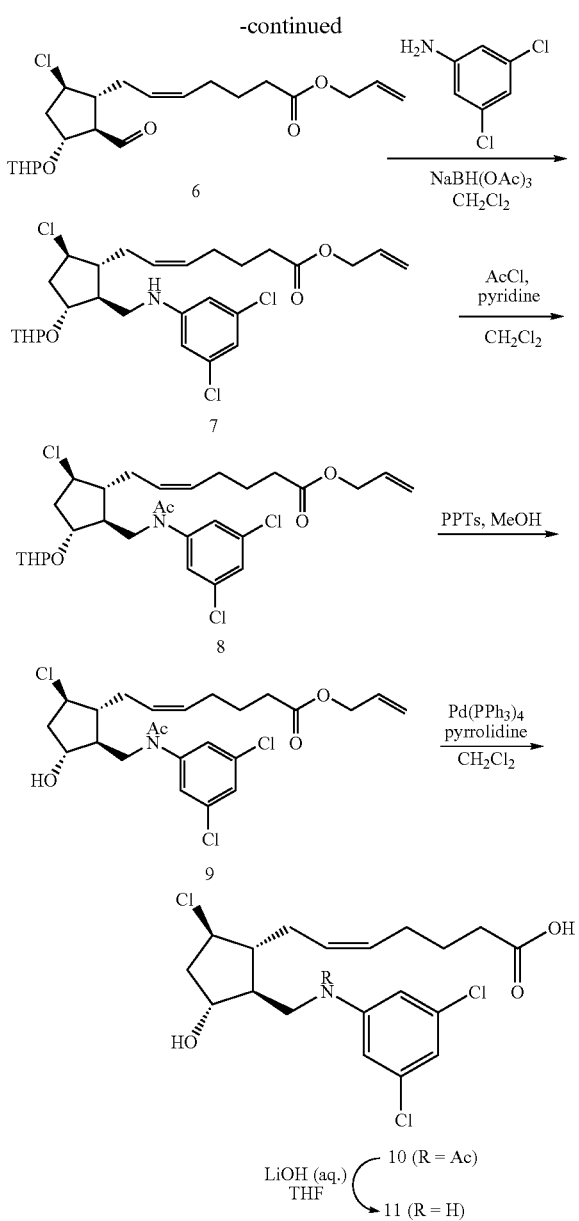

Synthetic Example 2

(Z)-7-((1R,2S,3R,5R)-2-{[Acetyl-(3,5-dichloro-phenyl)-amino]-methyl}-5-chloro-3-hydroxy-cyclopentyl)-hept-5-enoic acid (10)

Step 1. Oxidation of 1 to Give 6

DMSO (47 µL, 0.66 mmol) was added to a solution of oxalyl chloride (26 µL, 0.29 mmol) in CH$_2$Cl$_2$ (0.25 mL) at −78° C. After 15 min, a solution of alcohol 1 (125 mg, 0.31 mmol) in CH$_2$Cl$_2$ (0.5 mL+0.5 mL rinse) was added. After 15 min at −78° C., triethylamine (272 µL, 1.95 mmol) was added and the reaction was allowed to warm to room temperature. After 1 h at room temperature the reaction mixture was partitioned between saturated aqueous NaHCO$_3$ (3 mL) and CH$_2$Cl$_2$ (5 mL). The phases were separated and the aqueous phase was extracted with CH$_2$Cl$_2$ (2×5 mL). The combined extracts were dried (MgSO$_4$), filtered and concentrated in vacuo. Purification of the crude residue by flash column chromatography on silica gel (30% EtOAc/hexane) afforded 90 mg (72%) of aldehyde 6.

Step 2. Reduction Amination to Give 7

3,5-Dichloroaniline (57 mg, 0.35 mmol) was added to a solution of aldehyde 6 (90 mg, 0.23 mmol) in CH$_2$Cl$_2$ (1.75 mL) at room temperature. After 1 h, sodium triacetoxyborohydride (74 mg, 0.35 mmol) was added. After 18 h at room temperature, the reaction mixture was partitioned between saturated aqueous NaHCO$_3$ (5 mL) and CH$_2$Cl$_2$ (5 mL). The phases were separated and the aqueous phase was extracted with CH$_2$Cl$_2$ (2×5 mL). The combined extracts were washed with brine (5 mL), dried (MgSO$_4$), filtered and concentrated in vacuo. Purification of the crude residue by flash column chromatography on 4 g of silica gel (100% hexane→100% EtOAc, gradient) afforded 120 mg of an inseparable mixture of desired product 7 and 3,5-dichloroaniline which was used without further purification.

Step 3. Acylation of 7 to Give 8

Pyridine (17 µL, 0.21 mmol) and acetyl chloride (14 µL, 0.20 mmol) were added sequentially to a solution of impure amine 7 (~32 mg, ~0.059 mmol) in CH$_2$Cl$_2$ (0.1 mL) at 0° C. The reaction mixture was allowed to warm to room temperature. After 18 h at room temperature the reaction mixture was partitioned between saturated aqueous NaHCO$_3$ (2 mL) and CH$_2$Cl$_2$ (5 mL). The phases were separated and the aqueous phase was extracted with CH$_2$Cl$_2$ (5 mL). The combined extracts were washed with brine (2 mL), dried (MgSO$_4$), filtered and concentrated in vacuo. Purification of the crude residue by flash column chromatography on 4 g of silica gel (100% hexane →100% EtOAc, gradient) afforded 22 mg (64%) of acetate 8.

Step 4. Deprotection of 8 to Give 9

PPTs (1 mg, 0.004 mmol) was added to a solution of 8 (22 mg, 0.037 mmol) in methanol (0.38 mL) at room temperature under nitrogen. The solution was heated at 40° C. overnight, then cooled and concentrated in vacuo. Purification of the crude residue by flash column chromatography on 4 g of silica gel (100% hexane→100% EtOAc, gradient) afforded 19 mg (quant.) of alcohol 9.

Step 5. Deprotection of 9 to Give 10

Pyrrolidine (3 µL, 0.036 mmol) and tetrakis(triphenylphosphine)palladium(0) (2 mg, 0.0017 mmol) were added to a solution of allyl ester 9 (19 mg, 0.038 mmol) in CH$_2$Cl$_2$ (0.4 mL). After stirring overnight at room temperature, the reaction mixture was partitioned between aqueous HCl (1 N, 5 mL) and CH$_2$Cl$_2$ (5 mL). The phases were separated and the aqueous phase was extracted with CH$_2$Cl$_2$ (2×5 mL). The combined extracts were dried (MgSO$_4$), filtered and concentrated in vacuo. Purification of the crude residue by flash column chromatography on 4 g of silica gel (2×, 10% MeOH/CH$_2$Cl$_2$) afforded 5 mg (29%) of the title compound (10).

Synthetic Example 3

(Z)-7-{(1R,2S,3R,5R)-5-Chloro-2-[(3,5-dichloro-phenylamino)-methyl]-3-hydroxy-cyclopentyl}-hept-5-enoic acid (11)

Lithium hydroxide (21 µL of a 1.0 M aqueous solution, 0.021 mmol) was added to a solution of acetate 10 (2 mg, 0.004 mmol) in THF (0.2 mL). After stirring 3 d at room temperature, the reaction mixture was partitioned between aqueous HCl (1.0 N, 2 mL) and EtOAc (2 mL). The phases were separated and the aqueous phase was extracted with EtOAc (2 mL). The combined extracts were dried (MgSO$_4$), filtered and concentrated in vacuo to afford 1 mg (55%) of the title compound (11).

phase was dried (MgSO$_4$), filtered and concentrated in vacuo. Purification of the crude residue by chromatography on 12 g of silica gel (100% hexane→100% EtOAc, gradient) afforded 100 mg (57%) of desired product 13.

Step 4. Deprotection of 13 to Give 14

PPTs (1 mg, 0.004 mmol) was added to a solution of 13 (30 mg, 0.053 mmol) in methanol (0.5 mL) at room temperature under nitrogen. The solution was heated at 40° C. for 18 h, then cooled and concentrated in vacuo. Purification of the crude residue by chromatography on 4 g of silica gel (100% hexane→100% EtOAc, gradient) afforded 20 mg (78%) of alcohol 14.

Step 5. Saponification of 14 to Give 15

Lithium hydroxide (0.20 mL of a 1.0 M aqueous solution, 0.20 mmol) was added to a solution of ester 14 (20 mg, 0.042 mmol) in THF (0.2 mL). After stirring at 40° C. for 18 h, the reaction mixture was cooled and partitioned between aqueous HCl (0.1 N, 5 mL) and EtOAc (5 mL). The phases were separated and the aqueous phase was extracted with EtOAc (2×5 mL). The combined extracts were washed with brine (5 mL), dried (MgSO$_4$), filtered and concentrated in vacuo. Purification of the crude residue by chromatography on 4 g of silica gel (100% hexane→100% EtOAc, gradient) afforded 4 mg (21%) of the title compound (15).

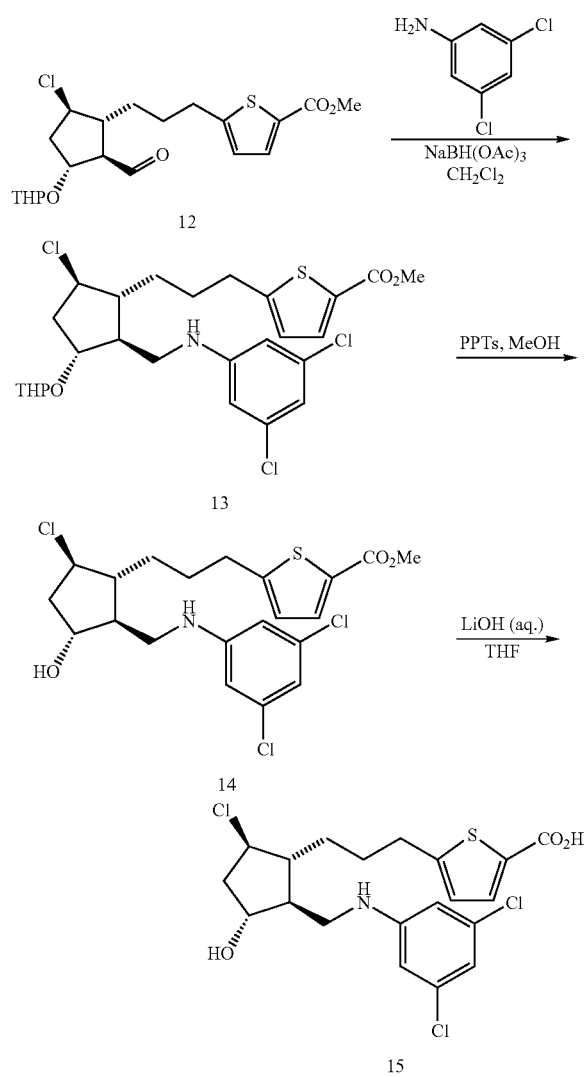

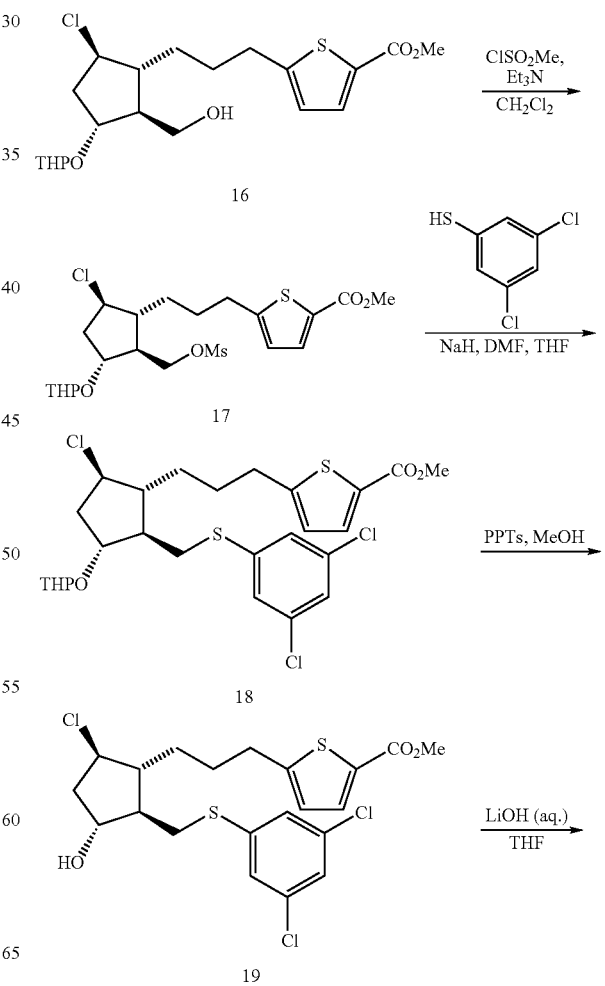

Synthetic Example 4

5-(3-((1R,2S,3R,5R)-5-chloro-2-((3,5-dichlorophenylamino)methyl)-3-hydroxycyclopentyl)propyl)-thiophene-2-carboxylic acid (15)

Step 1. Reduction Amination to Give 13

Sodium triacetoxyborohydride (132 mg, 0.62 mmol) was added in one portion to a solution of 3,5-dichloroaniline (101 mg, 0.63 mmol) was added to a solution of aldehyde 12 (see U.S. Provisional Patent Application No. 60/947,904, filed Jul. 3, 2007, which is incorporated by reference herein, 130 mg, 0.31 mmol) in CH$_2$Cl$_2$ (3.1 mL) at room temperature. After 3 d at room temperature, the reaction mixture was partitioned between saturated aqueous NaHCO$_3$ (5 mL) and CH$_2$Cl$_2$ (10 mL). The phases were separated and the aqueous phase was extracted with CH$_2$Cl$_2$ (2×10 mL). The combined organic

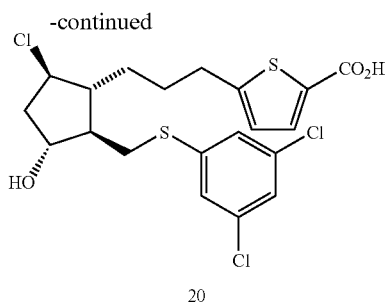

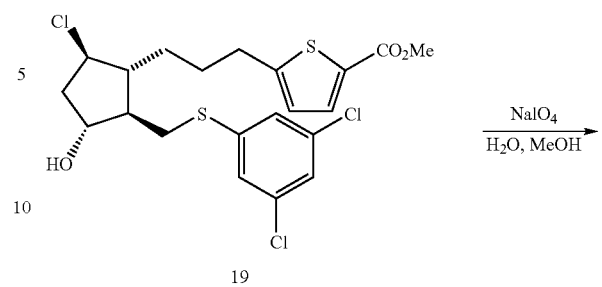

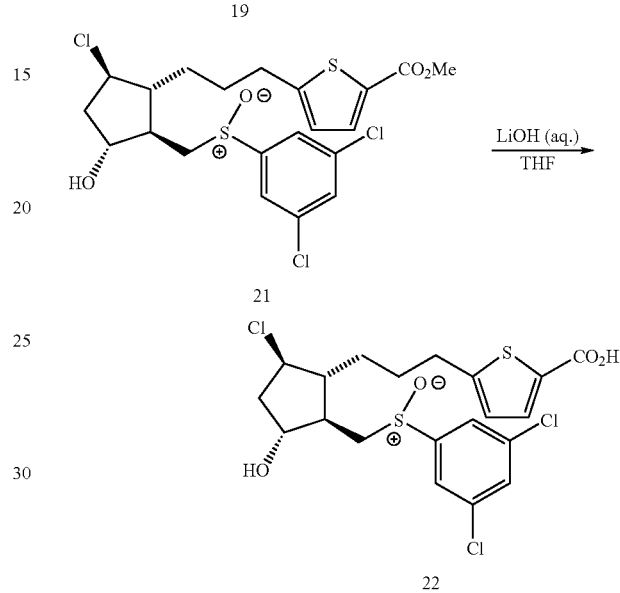

Synthetic Example 5

5-(3-((1R,2R,3R,5R)-5-chloro-2-((3,5-dichlorophenylthio)methyl)-3-hydroxycyclopentyl)propyl)-thiophene-2-carboxylic acid (20)

Step 1. Mesylation of 16 to Give 17

Triethylamine (25 µL, 0.18 mmol) and methanesulfonyl chloride (11 µL, 0.14 mmol) were added sequentially to a solution of alcohol 16 (see U.S. patent application Ser. No. 11/764,929 filed Jun. 19, 2007, which is incorporated by reference herein, 50 mg, 0.12 mmol) in $CH_2Cl_2$ (1.2 mL) at 0° C. The reaction mixture was allowed to warm to room temperature. After 3 h at room temperature, the reaction mixture was partitioned between saturated aqueous $NaHCO_3$ (5 mL) and $CH_2Cl_2$ (5 mL). The phases were separated and the aqueous phase was extracted with $CH_2Cl_2$ (2×5 mL). The combined extracts were washed with water (5 mL) and brine (5 mL), dried ($MgSO_4$), filtered and concentrated in vacuo to afford crude mesylate 17 which was used without further purification.

Step 2. Reaction of 17 to Give Thiol 18

Sodium hydride (60 wt % in oil, 17 mg, 0.42 mmol) was added to a solution of 3,5-dichlorobenzenethiol (75 mg, 0.42 mmol) in DMF (4 mL) in DMF (1 mL) at room temperature. After 30 min at room temperature, a solution of mesylate 17 (crude, ~0.12 mmol) in THF (1.2 mL) was added via syringe and the reaction mixture was heated at 60° C. After 18 h at 60° C., the reaction mixture was cooled and partitioned between water (10 mL) and EtOAc (20 mL). The phases were separated and the aqueous phase was extracted with EtOAc (2×10 mL). The combined organic phase was washed brine (15 mL), dried ($MgSO_4$), filtered and concentrated in vacuo. Purification of the crude residue by chromatography on 12 g of silica gel (100% hexane→100% EtOAc, gradient) afforded 10 mg (14% over two steps) of thiol 18.

Step 3. Deprotection of 18 to Give 19

PPTs (4.3 mg, 0.017 mmol) was added to a solution of 18 (10 mg, 0.017 mmol) in methanol (0.17 mL) at room temperature under nitrogen. The solution was heated at 40° C. overnight, then cooled and concentrated in vacuo. Purification of the crude residue by chromatography on 4 g of silica gel (100% hexane→100% EtOAc, gradient) afforded 8 mg (94%) of alcohol 19.

Step 4. Saponification of 19 to Give 20

In accordance with the procedures of example 4, step 5, ester 19 (8 mg, 0.016 mmol) was converted into 6 mg (77%) of the title compound (20).

Synthetic Example 6

5-(3-((1R,2R,3R,5R)-5-chloro-2-((3,5-dichlorophenylsulfinyl)methyl)-3-hydroxycyclopentyl)propyl)-thiophene-2-carboxylic acid (22)

Step 1. Oxidation of 19 to Give 21

A solution of sodium periodate (9 mg, 0.042 mmol) in water (0.2 mL) was added to a solution of thiol 19 (10 mg, 0.020 mmol) in MeOH (0.2 mL). After stirring at room temperature overnight, the reaction mixture was dried ($MgSO_4$), filtered and concentrated in vacuo. Purification of the crude residue by preparative thin layer chromatography on 4 g of silica gel (10% MeOH/$CH_2Cl_2$) afforded 3 mg (29%) of sulfoxide 21.

Step 2. Saponification of 21 to Give 22

Lithium hydroxide (0.05 mL of a 1.0 M aqueous solution, 0.05 mmol) was added to a solution of ester 21 (3 mg, 0.0059 mmol) in THF (0.05 mL) in a one dram vial and the vial was fitted with a screw top cap. After stirring room temperature for 5 d, the reaction mixture acidified with aqueous HCl (1.0 N, 1 mL) and extracted with $CH_2Cl_2$ (5 mL). The organic phase was dried ($MgSO_4$), filtered and concentrated in vacuo. Purification of the crude residue by preparative thin layer chromatography on 4 g of silica gel (10% MeOH/$CH_2Cl_2$) afforded 1 mg (34%) of the title compound (22).

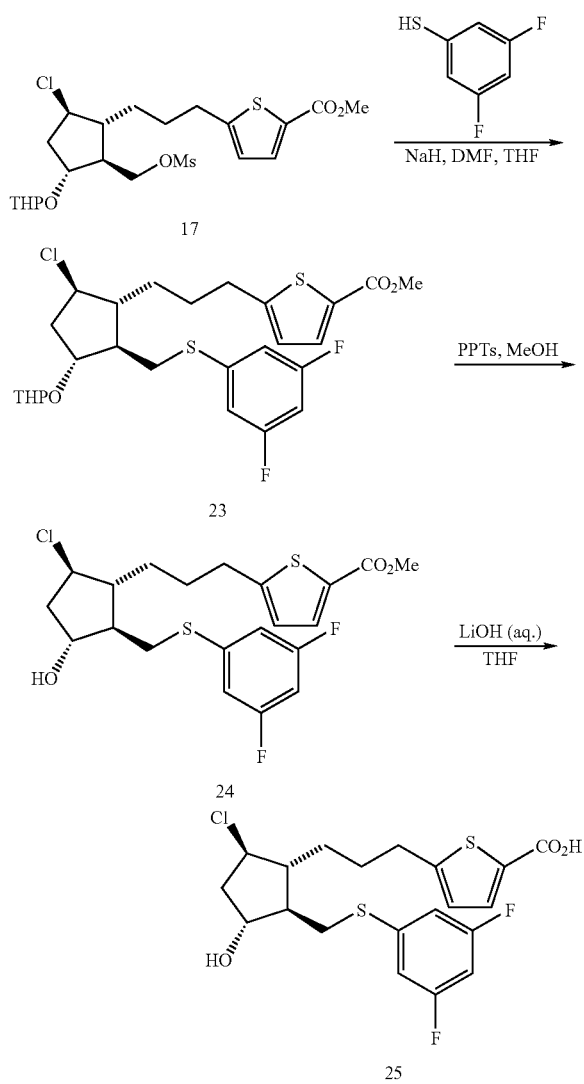

Synthetic Example 7

5-(3-(((1R,2R,3R,5R)-5-chloro-2-((3,5-difluorophenylthio)methyl)-3-hydroxycyclopentyl)propyl)-thiophene-2-carboxylic acid (25)

Step 1. Reaction of 17 to Give Thiol 23

Sodium hydride (60 wt % in oil, 115 mg, 2.88 mmol) was added to a solution of 3,5-difluorbenzenethiol (421 mg, 2.88 mmol) in DMF (20 mL) at room temperature. After 30 min at room temperature, a solution of mesylate 17 (crude, prepared from 16 (300 mg, 0.72 mmol) in accordance with the procedures of example 5, step 1, ~0.72 mmol) in THF (7.2 mL) was added via syringe and the reaction mixture was heated at 40° C. After 3 d at 40° C., the reaction mixture was cooled and partitioned between aqueous HCl (1.0 N, 10 mL) and EtOAc (50 mL). The phases were separated and the aqueous phase was extracted with EtOAc (2×10 mL). The combined organic phase was washed water (50 mL) and brine (50 mL), dried (MgSO$_4$), filtered and concentrated in vacuo to afford crude thiol 23 which was used without further purification.

Step 2. Deprotection of 23 to Give 24

PPTs (18 mg, 0.072 mmol) was added to a solution of thiol 23 (crude, ~0.72 mmol) in methanol (24 mL) at room temperature under nitrogen. The solution was heated at 40° C. overnight, then cooled and concentrated in vacuo. Purification of the crude residue by chromatography on 12 g of silica gel (100% hexane→100% EtOAc, gradient) afforded 7 mg (2%) of pure alcohol 24 and 125 mg of 24 contaminated with an impurity.

Step 3. Saponification of 24 to Give 25

Ester 24 (7 mg, 0.015 mmol) was converted into 4 mg (59%) of the title compound (25) in accordance with the procedures of example 4, step 5, with the following modifications: the extraction was carried out with CH$_2$Cl$_2$ instead of EtOAc and the chromatography gradient was CH$_2$Cl$_2$→10% MeOH/CH$_2$Cl$_2$.

The α-chain A may be modified may be varied by following or adapting procedures found in U.S. patent application Ser. No. 11/764,929, filed Jun. 19, 2007, which is expressly incorporated by reference herein, wherein an analog of the Corey lactone is used as the precursor to a Wittig reaction to install all the atoms of the α-chain; other Wittig reactions and the preparation of the requisite phosphonates are described by Collect. Czech. Chem. Commun. 1994, 58, 138-148, and Collect. Czech. Chem. Commun. 1994, 59, 2533-2544. Alternatively, the intermediate Corey lactone analog may be reduced to the corresponding primary alcohol, which may then be manipulated by methods known in the art to compounds bearing a heteroatom at the 5th (by alkylation of the alcohol or the derived thiol), 4th (by lengthening the chain by one atom (e.g. by homologation via the corresponding aldehyde)) or 6th (by shortening the chain by one atom (e.g. by ozonolysis of an enol ether derived from the corresponding aldehyde)) atom from the acid terminus.

Different J$^1$, J$^2$, and U$^1$ substituents may be obtained by following or adapting procedures found in the following documents, all of which are expressly incorporated by reference herein:

U.S. patent application Ser. No. 11/764,929;

U.S. patent application Ser. No. 11/738,307, filed on Apr. 20, 2007;

U.S. patent application Ser. No. 11/690,678, filed on May 23, 2007;

U.S. patent application Ser. No. 11/742,987 filed on May 1, 2007; and

U.S. patent application Ser. No. 11/747,478, filed on May 11, 2007.

Analogs of 3,5-dichloroaniline may be obtained commercially, or prepared from commercially available nitroaryl compounds by reduction. Other aromatic (or heteroaromatic) amines may be prepared from the corresponding aryl (or heteroaryl) halide or sulfonate by using benzophenone imine and following or adapting procedures described by Buchwald, et al. (e.g. J. Org. Chem. 2006, 71, 430-433 and Tetrahedron Lett. 1997, 38, 6367-6370). Alternatively, the intermediate hydroxymethyl moiety (in compounds such as 1 and its analogs) may be converted to the corresponding primary amine, for example, via a sulfonate intermediate reacting with sodium azide, followed by reduction to a primary amine. This amine may then be arylated (or heteroarylated) via the Buchwald procedure described above.

Analogs of 3,5-dichlorobenzenethiol may be obtained commercially. Other aromatic (or heteroaromatic) sulfides may be prepared from the corresponding aryl (or heteroaryl) halide or sulfonate and a silyl-SH or alkyl-SH analog (followed by desilylation or dealkylation to reveal the requisite thiol) by following or adapting procedures described by Buchwald (e.g. *Tetrahedron* 2004, 60, 7397-7403) and Hartwig (e.g. *J. Am. Chem. Soc.* 2006, 128, 2180-2181). Alternatively, the nucleophilic aromatic substitution of NaSH with an appropriate aryl or heteroaryl halide may be accomplished by adapting methods known in the art (e.g. see Peach, in Patai, "The Chemistry of the Thiol Group," pt. 2, pp 735-744, Wiley, New York, 1974). In another alternative approach, the intermediate hydroxymethyl moiety (in compounds such as 1 and its analogs) may be converted to the corresponding thiol (e.g. via a sulfonate intermediate reacting with sodium thioacetate, followed by deacylation). This thiol then may be arylated (or heteroarylated) on sulfur using an appropriate aryl (or heteroaryl) halide or sulfonate (see Buchwald and Hartwig references above).

Oxidation of the sulfur atom to either to the sulfoxide or the sulfone analog may be readily accomplished by methods known in the art.

The compounds disclosed herein are believed to be selective prostaglandin $EP_2$ agonists, and are thus useful for the treatment of glaucoma, ocular hypertension, and other diseases or conditions.

In Vitro Testing

U.S. patent application Ser. No. 11/553,143, filed on Oct. 26, 2006, incorporated by reference herein, describes the methods used to obtain the in vitro data in the table below.

| Structure | EP2 data | | | EP4 data | | Other Receptors (EC50 in nM) | | | | | |
| --- | --- | --- | --- | --- | --- | --- | --- | --- | --- | --- | --- |
| | flipr EC50 | cAMP EC50 | Ki | flipr EC50 | KI | hFP | hEP1 | hEP3A | hTP | hIP | hDP |
| (structure 1) | 3364 | 0.4 | 22 | >10000 | 376 | NA | NA | >10000 | 1718 | >10000 | >10000 |
| (structure 2) | 6371 | 29 | 2090 | NT | >10000 | NA | NA | | 2683 | >10000 | NA |
| (structure 3) | 135 | 0.5 | 18 | >10000 | 1034 | NA | NA | >10000 | >10000 | >10000 | NA |
| (structure 4) | >10000 | 110 | 336 | NT | NA | NA | NA | NA | NA | NA | NA |

-continued

| Structure | EP2 data | | | EP4 data | | Other Receptors (EC50 in nM) | | | | | |
|---|---|---|---|---|---|---|---|---|---|---|---|
| | flipr EC50 | cAMP EC50 | Ki | flipr EC50 | KI | hFP | hEP1 | hEP3A | hTP | hIP | hDP |
| (structure with Cl, OH, thiophene carboxylate, S-3,5-dichlorophenyl) | 59 | 0.11 | 0.3 | >10000 | 828 | NA | NA | NA | NA | NA | NA |
| (structure with Cl, OH, thiophene carboxylate, S(O)-3,5-dichlorophenyl sulfoxide) | 101 | 0.4 | 12 | >10000 | | NA | NA | NA | 4209 | NA | NA |
| (structure with Cl, OH, thiophene carboxylate, S-3,5-difluorophenyl) | 850 | 1.3 | 9 | >10000 | 2332 | NA | NA | NA | | NA | |

IN VIVO EXAMPLES

U.S. Pat. No. 7,091,231 describes the methods used for these in vivo tests.

In Vivo Example 1

5-(3-((1R,2R,3R,5R)-5-chloro-2-((3,5-dichlorophenylthio)methyl)-3-hydroxycyclopentyl)propyl)-thiophene-2-carboxylic acid (20) was tested in normotensive dogs at 0.01%, dosing once daily for 5 days. The maximum intraocular pressure (IOP) decrease from baseline was 6.3 mmHg (35%) at 6 h; the maximum ocular surface hyperemia (OSH) score was 1.7 at 52 h.

In Vivo Example 2

The composition and dosage regimen of In vivo example 1 was also tested in laser-induced hypertensive monkeys, using one single day dose. At 0.01%, the maximum IOP decrease from baseline was 13.9 mmHg (40%) at 24 h.

In Vivo Example 3

The composition and dosage regimen of In vivo example 1 may also be used to reduce IOP in humans.

The foregoing description details specific methods and compositions that can be employed to practice the present invention. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound having a formula

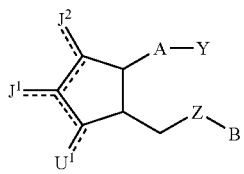

or a pharmaceutically acceptable salt thereof;
wherein a dashed line represents the presence or absence of a bond;
Y is an organic acid functional group, or an amide or ester thereof consisting of up to 14 carbon atoms; or Y is hydroxymethyl or an ether thereof consisting of up to 14 carbon atoms; or Y is a tetrazolyl functional group;
A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced by S or O; or A is —(CH$_2$)$_m$—Ar—(CH$_2$)$_o$— wherein Ar is interarylene or heterointerarylene, the sum of m and o is 1, 2, 3, or 4, and wherein one CH$_2$ may be replaced by S or O;
U$^1$ is independently hydrogen; OH; O; S; F; Cl; Br; I; CN; or O-alkyl consisting of 1, 2, 3, 4, 5 or 6 carbon atoms;
J$^1$ and J$^2$ are independently hydrogen; F; Cl, Br; I; O; OH; CN; O-alkyl consisting of 1, 2, 3, 4, 5 or 6 carbon atoms; alkyl consisting of 1, 2, 3, 4, 5, or 6 carbon atoms; or CF$_3$;
Z is S, SO, SO$_2$, NR, NCOR, or NSO$_2$R, wherein R is H or C$_{1-6}$ hydrocarbyl, and
B is aryl or heteroaryl.

2. A compound which is a carboxylic acid or a bioisostere thereof, said carboxylic acid having a structure

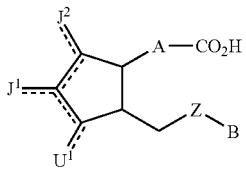

or a pharmaceutically acceptable salt thereof;
wherein a dashed line represents the presence or absence of a bond;
A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced by S or O; or A is —(CH$_2$)$_m$—Ar—(CH$_2$)$_o$— wherein Ar is interarylene or heterointerarylene, the sum of m and o is 1, 2, 3, or 4, and wherein one CH$_2$ may be replaced by S or O;
U$^1$ is independently hydrogen; OH; O; S; F; Cl; Br; I; CN; or O-alkyl consisting of 1, 2, 3, 4, 5 or 6 carbon atoms;
J$^1$ and J$^2$ are independently hydrogen; F; Cl, Br; I; O; OH; CN; O-alkyl consisting of 1, 2, 3, 4, 5 or 6 carbon atoms; alkyl having 1, 2, 3, 4, 5 or 6 carbon atoms; or CF$_3$;
Z is S, SO, SO$_2$, NR, NCOR, or NSO$_2$R, wherein R is H or C$_{1-6}$ hydrocarbyl, and
B is aryl or heteroaryl.

3. The compound of claim 1 wherein Y is selected from CO$_2$R$^2$, CON(R$^2$)$_2$, CON(OR$^2$)R$^2$, CON(CH$_2$CH$_2$OH)$_2$, CONH(CH$_2$CH$_2$OH), CH$_2$OH, P(O)(OH)$_2$, CONHSO$_2$R, SO$_2$N(R$^2$)$_2$, SO$_2$NHR$^2$,

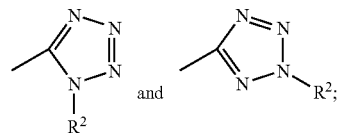

wherein R$^2$ is independently H, C$_1$-C$_6$ alkyl, unsubstituted phenyl, or unsubstituted biphenyl.

4. The compound of claim of claim 3 wherein B is substituted or unsubstituted phenyl or substituted or unsubstituted pyridinyl.

5. The compound of claim of claim 4 wherein B is substituted or unsubstituted phenyl.

6. The compound of claim 4 having the formula

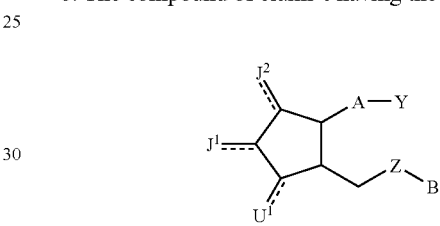

or a pharmaceutically acceptable salt thereof.

7. The compound of claim 6 wherein B is phenyl having from 0 to 4 substituents independently selected from F, Cl, Br, C$_{1-3}$ alkyl, and C$_{1-3}$ alkoxy.

8. The compound of claim 4 wherein A is 5-(3-propyl) thiophen-2-yl.

9. The compound of claim 4 wherein A is (Z)-6-hex-4-enyl.

10. The compound of claim 4 wherein U$^1$ is OH.

11. The compound of claim 4 wherein J$^1$ is hydrogen.

12. The compound of claim 4 wherein J$^2$ is Cl.

13. The compound of claim 7 wherein Z is S.

14. The compound of claim 7 wherein Z is SO.

15. The compound of claim 7 wherein Z is NH.

16. The compound of claim 7 wherein Z is NCOCH$_3$.

17. The compound of claim 6 wherein J$^1$ is hydrogen; U$^1$ and J$^2$ are independently selected from F, Cl, and OH; and Z is S, SO, NH, or NCOR.

18. A method of reducing intraocular pressure comprising administering a compound of claim 1 to a mammal in need thereof.

19. A method of treating glaucoma comprising administering a compound of claim 1 to a mammal in need thereof.

* * * * *